US012077564B2

(12) United States Patent
Bond et al.

(10) Patent No.: US 12,077,564 B2
(45) **Date of Patent: *Sep. 3, 2024**

(54) HIV/SIV NEF FUSION PROTEINS FOR EXOSOME TARGETED EXPRESSION

(71) Applicant: MOREHOUSE SCHOOL OF MEDICINE, Atlanta, GA (US)

(72) Inventors: Vincent C. Bond, Stone Mountain, GA (US); Michael Powell, Douglasville, GA (US); Ming Bo Huang, Atlanta, GA (US); Syed Ali, Lafayette, LA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 185 days.

This patent is subject to a terminal disclaimer.

(21) Appl. No.: 17/305,749

(22) Filed: Jul. 14, 2021

(65) Prior Publication Data

US 2021/0355172 A1 Nov. 18, 2021

Related U.S. Application Data

(63) Continuation of application No. 16/458,218, filed on Jul. 1, 2019, now Pat. No. 11,098,087, which is a continuation of application No. 16/034,237, filed on Jul. 12, 2018, now Pat. No. 10,414,804, which is a continuation of application No. 15/660,572, filed on Jul. 26, 2017, now Pat. No. 10,053,496, which is a continuation of application No. 13/327,244, filed on Dec. 15, 2011, now Pat. No. 9,777,042.

(51) Int. Cl.

| | |
|---|---|
| ***C07K 14/16*** | (2006.01) |
| ***A61K 9/127*** | (2006.01) |
| ***A61K 38/16*** | (2006.01) |
| ***C07K 14/005*** | (2006.01) |
| *A61K 38/00* | (2006.01) |
| *A61K 39/00* | (2006.01) |
| *A61K 39/39* | (2006.01) |
| *A61K 45/06* | (2006.01) |
| *C12N 15/00* | (2006.01) |
| *C12P 21/02* | (2006.01) |
| *G01N 33/543* | (2006.01) |
| *G01N 33/566* | (2006.01) |

(52) U.S. Cl.

CPC ............ *C07K 14/163* (2013.01); *A61K 9/127* (2013.01); *A61K 38/162* (2013.01); *C07K 14/005* (2013.01); *A61K 38/00* (2013.01); *A61K 39/39* (2013.01); *A61K 2039/55555* (2013.01); *A61K 45/06* (2013.01); *C07K 2319/00* (2013.01); *C07K 2319/055* (2013.01); *C07K 2319/50* (2013.01); *C07K 2319/60* (2013.01); *C12N 15/00* (2013.01); *C12N 2740/16311* (2013.01); *C12N 2740/16322* (2013.01); *C12P 21/02* (2013.01); *G01N 33/543* (2013.01); *G01N 33/566* (2013.01)

(58) Field of Classification Search

CPC .............. C07K 14/163; C07K 2319/00; C12N 2740/16311

See application file for complete search history.

(56) References Cited

U.S. PATENT DOCUMENTS

| | | | | |
|---|---|---|---|---|
| 8,603,490 | B2 | 12/2013 | Ruprecht | |
| 10,053,496 | B2 * | 8/2018 | Bond .................. | C07K 14/163 |
| 2011/0142912 | A1 | 6/2011 | Moser et al. | |

OTHER PUBLICATIONS

Ali, S. A., et al., 2010, Genetic Characterization of HIV Type 1 Nef-Induced Vesicle Secretion, AIDS Res. Human Retrovir. 26(2):173-192 (published Feb. 15, 2010).*

Ali et al., "Genetic Characterization of HIV Type 1 Nef-Induced Vesicle Secretion," AIDS Research and Human Retroviruses, 2010, pp. 173-192, vol. 26—No. 2.

Campbell et al., "HIV-1 Nef Protein Is Secreted Into Vesicles That Can Fuse With Target Cells and Virions," Ethnicity & Disease, Spring 2008, pp. S2-14-S2-19, vol. 18.

Lenassi et al., "HIV Nef is secreted in exosomes and triggers apoptosis in bystander CD4+ T cells," Traffic, Jan. 2010, pp. 110-122, vol. 11—No. 1.

Raposo et al., "B Lymphocytes Secrete Antigen-presenting Vesicles", J. Exp. Med., vol. 183, pp. 1161-1172 (1996).

Zitvogel el al., "Eradication of established murine tumors using a novel cell-free vaccine: dendritic cell derived exosomes", Nature Medicine, vol. 4, No. 5, pp. 594-600 (1998).

Tan et al., "The application of exosomes as a nanoscale cancer vaccine", International Journal of Nanomedicine, vol. 5, pp. 889-900 (2010).

Izquierdo-Useros et al., "HIV and Mature Dendritic Cells: Trojan Exosomes Riding the Trojan Horse?", PLoS Pathogens, vol. 6, Issue 3 (2010).

James et al., "Extracellular Nef Protein Targets CD4+ T Cells for Apoptosis by Interacting with CXCR4 Surface Receptors", Journal of Virology, vol. 78, No. 6, pp. 3099-3109 (2004).

Piguet et al., "HIV-1 Nef protein binds to the cellular protein PACS-1 to downregulate class I major histocompatibility complexes", Nat. Cell Biol., vol. 2, Issue 3, pp. 163-167 (2000).

Geyer et al., "Structure of the Anchor-Domain of Myristoylated and Non-myristoylated HIV-1 Nef Protein", J. Mol. Biol., vol. 289, Issue 1, pp. 123-138 (1999).

(Continued)

*Primary Examiner* — Jeffrey S Parkin

(74) *Attorney, Agent, or Firm* — Ping Wang; Kalos Athena Wang PLLC

(57) ABSTRACT

The present application relates to methods of producing exosomes. The application also provides a method for preparing a protein composition comprising culturing an exosome-producing cell expressing a Nef-fusion protein comprising a Nef-derived peptide fused to a protein of interest; isolating exosomes from the exosome-producing cell culture; and purifying the protein of interest from the isolated exosomes. The application further discloses compositions that comprise exosomes containing the Nef-fusion protein, as well as methods of using the Nef-fusion protein and exosomes containing the Nef-fusion protein.

11 Claims, 11 Drawing Sheets

Specification includes a Sequence Listing.

(56) References Cited

OTHER PUBLICATIONS

Thery et al., "Proteomic Analysis of Dendritic Cell-Derived Exosomes: A Secreted Subcellular Compartment Distinct from Apoptotic Vesicles", J. Immunol., vol. 166, Issue 12, pp. 7309-7318 (2001).
Aupeix et al., "The Significance of Shed Membrane Particles during Programmed Cell Death In Vitro, and In Vivo, in HIV-1 Infection", J. Clin. Invest., vol. 99, No. 7, pp. 1546-1554 (1997).
Huang et al., "Characterization of Nef-CXCR4 Interactions Important for Apoptosis Induction", J. Virol., vol. 78, No. 20, pp. 11084-11096 (2004).
Di Bonito, P., et al., 2009, Anti-tumor CD8+ T cell immunity elicited by HIV-1-based virus-like particles incorporating HPV-16 E7 protein, Virol. 395:45-55.
Echarri, A., et al., 1996, Human Immunodeficiency virus (HIV) Nef is an RNA binding protein in cell-free systems, J. Mol. Bioi. 262:640-651.
Singh, R. K., et al., Dec. 2009, An MHC-1 cytoplasmic domain/HIV-1 Nef fusion protein binds directly to the u subunit of the AP-1 endosomal coat complex, PLoS One 4(12):e8364 (1-7).
Vader, P., et al., 2016, Extracellular vesicles for drug delivery, Adv. Drug Deliv. Rev. 106: 148-156.
Ferguson, S. W., and J. Nguyen, 2016, Exosomes as therapeutics: The implications of molecular composition and exosomal heterogeneity, J. Controlled Release 228: 179-190.
Gyorgy, B., et al., 2015, Therapeutic Applications of Extracellular Vesicles: Clinical Promise and Open Questions, Annu. Rev. Pharmacol. Toxicol. 55:439-464.
Johnsen, K. B., et al., 2014, A comprehensive overview of exosomes as drug delivery vehicles-Endogenous nanocarriers for targeted cancer therapy, Biochim. Biophys. Acta 1846:75-87.
Lakhal, S., and M.J.A. Wood, 2011, Exosome nanotechnology; An emerging paradigm shift in drug delivery, Bioessays 33:737-741.
Niederman, T. M. J., et al., Jul. 1991, Simian immunodeficiency virus negative factor supresses the level of viral mRNA in COS cells, J. Viral, 65(7):3538-3546.
Uni ProtKB-088077 (088077_SIV), Simian Immunodeficiency Virus Nef protein, Nov. 1, 1996, pp. 1-2.
Ali, S. A., et al., 2010, Genetic characterization of HIV type 1 Net-induced vesicle secretion, AIDS Res. Human Retrovir. 26(2):173-192.
Wu, C., et al., 2007, Dual-reporter assay using two secreted luciferase genes, BioTech. 42(3):290-291.
File history of U.S. Appl. No. 13/327,244, filed Dec. 15, 2011.
File history of U.S. Appl. No. 15/660,572, filed Jul. 26, 2017.
File history of U.S. Appl. No. 16/034,237, filed Jul. 12, 2018.
File history of U.S. Appl. No. 16/458,218, filed Jul. 1, 2019.

* cited by examiner

Fig. 1A
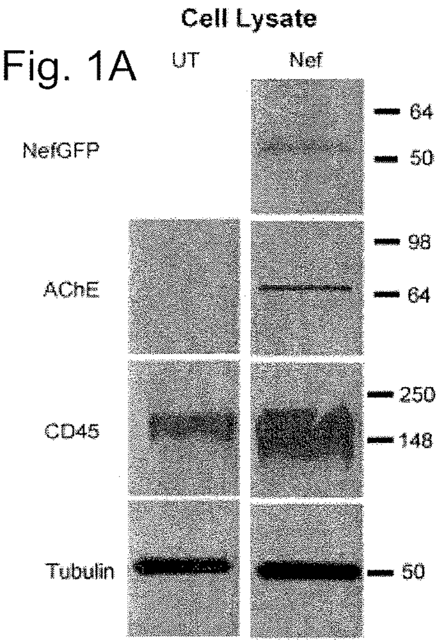
Fig. 1B
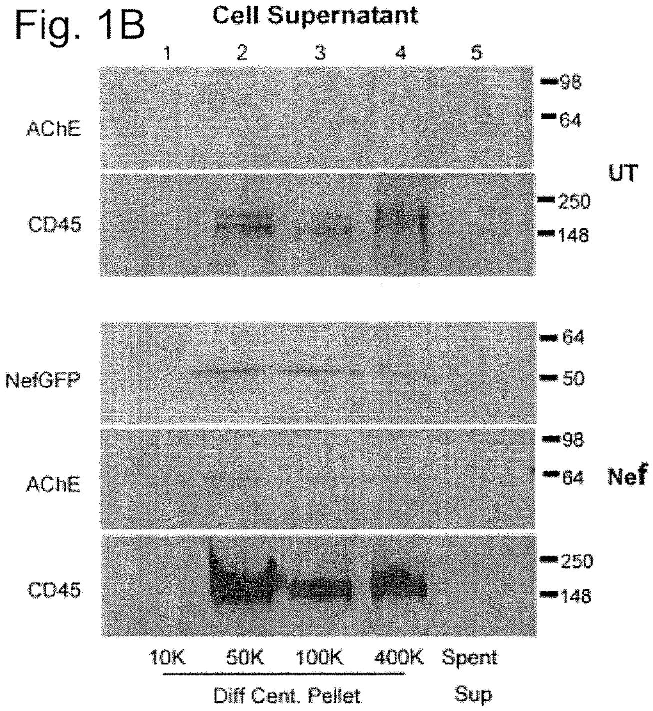
Fig. 1C
| TREATMENT | CELL LYSATES | | |
|---|---|---|---|
| | NEF | AChE | CD45 |
| Untransfected (UT) | ------- | 1519 ± 8 | 51428 ± 101 |
| NEF-Transfected (NT) | 33460 ± 74 | 16467 ± 47 | 81384 ± 73 |
| *p*-Value (UT vs. NT) | ------ | 0.00125 | 0.05061 |
| TREATMENT | SUPERNATANTS | | |
| | NEF | AChE | CD45 |
| Untransfected (UT) | ------ | 239 ± 7 | 2936 ± 6 |
| NEF-Transfected (NT) | 3848 ± 55 | 992 ± 6 | 6774 ± 11 |
| *p*-Value (UT vs. NT) | ------- | 0.00074 | 0.00102 |

| Antibody Probe | Untransfected Jurkat Cells | | | |
|---|---|---|---|---|
| | Cell Lysate | Supernatant | Diff. Cent. | Gradient |
| Nef<br>GFP<br>Alix | 0<br>0<br>4383 ± 10.3 | 0<br>0<br>2088 ± 8.9 | 0<br>0<br>3352 ± 0.1 | 0<br>0<br>3278 ± 0.3 |
| Ab. Probe | Nef Transfected Jurkat Cells | | | |
| Nef<br>GFP<br>Alix<br>*p*-value | 27790 ± 4.5<br>58381 ± 11<br>24091 ± 32<br>0.005 | 31068 ± 0.98<br>61326 ± 1.6<br>27132 ± 13<br>>.001 | 31020 ± 0.16<br>38128 ± 0.4<br>19276 ± 1<br>0.0023 | 18702 ± 1.7<br>42030 ± 0.9<br>19618 ± 0.2<br>>.001 |

|   | Basic amino acid 1 | helix-1 | | |
|---|---|---|---|---|
| 1 | MGGKWSKSSV | IGWPAVRERM | RRAEPAADGV | GAVSRDLEKH |
|   | Myristoylation | Basic amino acid 2 | | helix-2 |
|   |   | Apoptotic Motif 1 | PACS | SH3 domain |
| 41 | GAITSSNTAA | TNAACAWLEA | QEEEEVGFPV | TPQVPLRPMT |
|   | Membrane targeting domain | | SMR | |
| 80 | YKAAVDLSHF | LKEKGGLEGL | IHSQRRQDIL | DLWIYHTQGY |
|   |   | PPT | | |
| 120 | FPDWQNYTPG | PGVRYPLTFG | WCYKLVPVEP | DKVEEANKGE |
|   |   | Apoptotic Motif 2 | | |
| 160 | NTSLLHPVSL | HGMDDPEREV | LEWRFDSRLA | FHHVARELHP |
| 200 | EYFKNCGAG | (SEQ ID NO:39) | | |

FIG. 5A

```
Myristoylation              Alpha helix
MGGAISMRRS  RPSGDLRQRL  LRARGETYGR  LLGEVEDGYS
          10          20          30          40
     BAA-1        BAA-2
QSPGGLDKGL  SSLSCEGQKY  NQGQYMNTPW  RNPAEEREKL
          50          60          70          80
       PACS            SMR     Polypurine tract
AYRKQNMDDI  DEEDDDLVGV  SVRPKVPLRT  MSYKLAIDMS
          90         100         110         120
      Acidic residues
HFIKEKGGLE  GIYYSARRHR  ILDIYLEKEE  GIIPDWQDYT
         130         140         150         160
LGPGIRXPKT  FGWLWKLVPV  NVSDEAQEDE  EHYLMHPAQT
         170         180         190         200
SQWDDPWGEV  LAWKFDPTLA  YTYEAYVRYP  EEFGSKSGLS
         210         220         230         240
EEEVRRRLTA  RGLLNMADKK  ETR   (SEQ ID NO:2)
         250         260
```

FIG. 5B

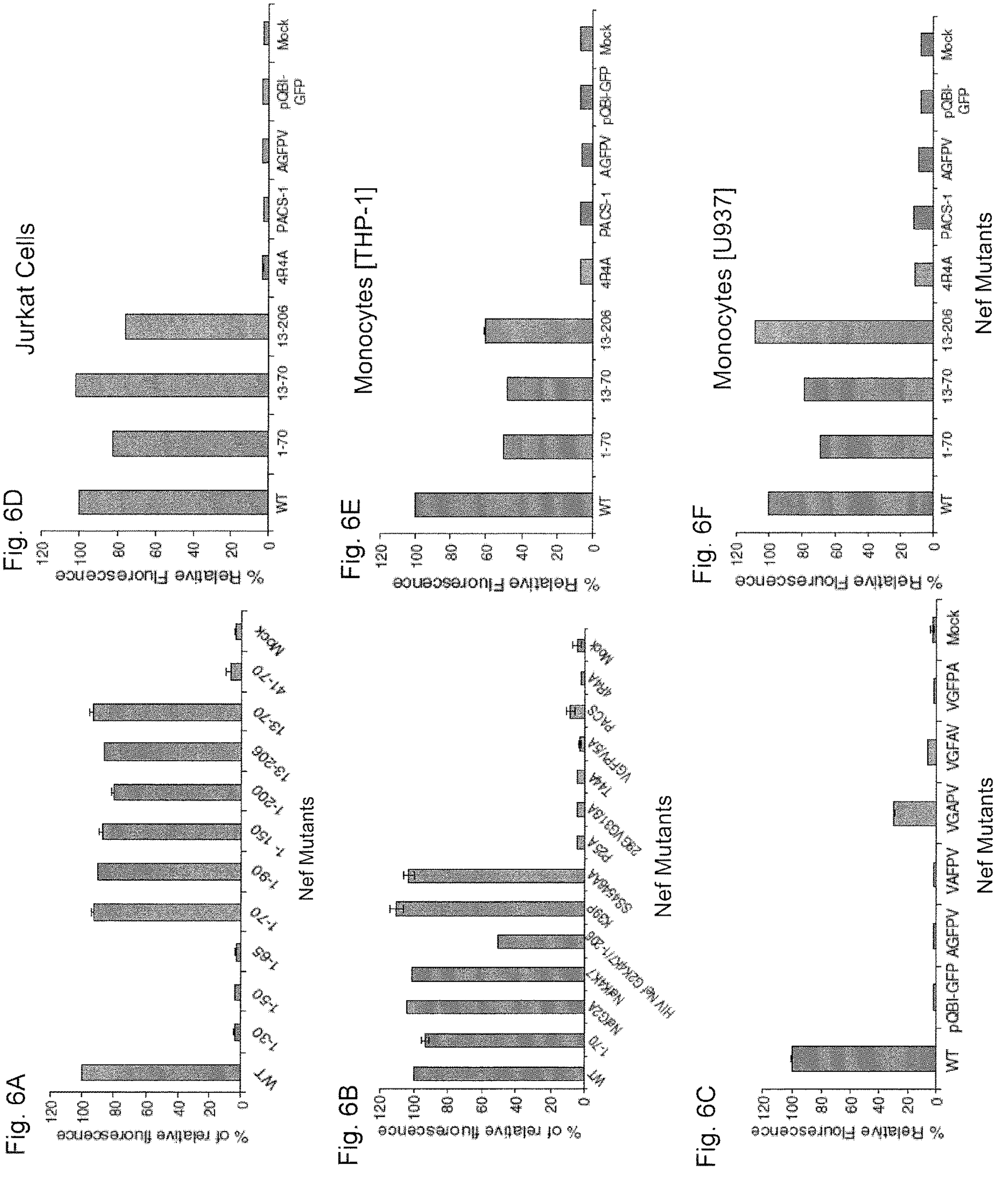
Fig. 6A
% of relative fluorescence
WT 1-30 1-50 1-65 1-70 1-90 1-150 1-200 13-206 13-70 41-70 Mock
Nef Mutants
Fig. 6B
% of relative fluorescence
Nef Mutants
Fig. 6C
% Relative Flourescence
WT pQBI-GFP AGFPV VAFPV VGAPV VGFAV VGFPA Mock
Nef Mutants
Fig. 6D
Jurkat Cells
% Relative Fluorescence
WT 1-70 13-70 13-206 4R4A PACS-1 AGFPV pQBI-GFP Mock
Fig. 6E
Monocytes [THP-1]
% Relative Fluorescence
WT 1-70 13-70 13-206 4R4A PACS-1 AGFPV pQBI-GFP Mock
Fig. 6F
Monocytes [U937]
% Relative Flourescence
WT 1-70 13-70 13-206 4R4A PACS-1 AGFPV pQBI-GFP Mock
Nef Mutants

PACS/SMR Alignment

| | | |
|---|---|---|
| HIV1 A1 | QEEEE-VGFPV | (SEQ ID NO:40) |
| HIV1 A2 | QEEEEEVGFPV | (SEQ ID NO:41) |
| HIV1 B | QEEEE-VGFPV | (SEQ ID NO:42) |
| HIV1 C | QEEEEEVGFPV | (SEQ ID NO:43) |
| HIV1 D | QEEEEEVGFPV | (SEQ ID NO:44) |
| HIV1 F1 | QEEEE-VGFPV | (SEQ ID NO:45) |
| HIV1 F2 | QEDEE-VGFPV | (SEQ ID NO:46) |
| HIV1 G | QQEDSEVGFPV | (SEQ ID NO:47) |
| HIV1 H | QEEEEEVGFPV | (SEQ ID NO:48) |
| HIV1 J | QTEEE-VGFPV | (SEQ ID NO:49) |
| HIV1 K | QEEEE-VGFPV | (SEQ ID NO:50) |
| HIV1 N | QEEEEEVGFPV | (SEQ ID NO:51) |
| HIV1 O | HQDEE-VGFPV | (SEQ ID NO:52) |

FIG. 7

Coomassie Stained Gel

Western Analysis

| Blot/Ab \ Lane (1-6) | WT Nef-GFP | GFP | PACS-GFP | AGFPV-GFP | 4R4A-GFP | UT |
|---|---|---|---|---|---|---|
| (A)Nef mAb | 383 ± 4 | 0 | 1704 ± 2.6 | 1761 ± 6 | 1586 ± 0.2 | 0 |
| (B)GFP mAb | 108 ± 0.2 | 963 ± 0.05 | 1136 ± 1.5 | 1043 ± 0.4 | 647 ± 0.9 | 0 |
| (C)Tubulin mAb | 3802 ± 0.2 | 3849 ± 0.2 | 3928 ± 0.8 | 3750 ± 0.2 | 3740 ± 0.2 | 2680 ± 0.2 |

HIV/SIV NEF FUSION PROTEINS FOR EXOSOME TARGETED EXPRESSION

This application is a Continuation of U.S. application Ser. No. 16/458,218, filed Jul. 1, 2019, which is a Continuation of U.S. application Ser. No. 16/034,237, filed Jul. 12, 2018, now U.S. Pat. No. 10,414,804, which is a Continuation of U.S. application Ser. No. 15/660,572, filed Jul. 26, 2017, now U.S. Pat. No. 10,053,496, which is a Continuation Application of U.S. application Ser. No. 13/327,244, filed Dec. 15, 2011, now U.S. Pat. No. 9,777,042. The entirety of the aforementioned application is incorporated herein by reference.

FIELD

The present application relates to methods of producing exosomes, and exosome targeted expression of fusion proteins with predefined sequences of interest for the therapeutic and diagnostic uses.

BACKGROUND

Exosomes are small vesicles 40-100 nm in diameter, that are secreted by a number of different cell types for communicating with other cells via the proteins and ribonucleic acids they carry. Depending on their cellular origin, exosomes carry a uniquely distinct profile of proteins, which can trigger signaling pathways in other cells and/or transfer exosomal products into other cells by exosomal fusion with cellular plasma membranes. The protein composition of exosomes is distinct from that of other organelles, including early endosomes and plasma membranes, more closely resembling that of late endosomes or multivesicular bodies, (MVBs).

Exosome release has been demonstrated from different cell types in varied physiological contexts. For example, it has been demonstrated that B lymphocytes release exosomes carrying class II major histocompatibility complex molecules, which play a role in antigenic presentation (Raposo et al., *J. Exp. Med.,* 183:1161, 1996). Similarly, it has been demonstrated that dendritic cells produce exosomes (i.e., dexosomes, Dex), which play a role in immune response mediation, particularly in cytotoxic T lymphocyte stimulation (Zitvogel et al., *Nature Medicine,* 4:594, 1998). Further, it has also been demonstrated that tumor cells secrete specific exosomes (i.e., texosomes, Tex) carrying tumor antigens in a regulated manner, which can present these antigens to antigen presenting cells. The application of exosomes for use as cancer vaccines has been reviewed by Tan et al., *Int. J. Nanomed.,* 5:889-900, 2010.

Nef is a protein expressed by primate lentiviruses, such as HIV and SIV. Nef is known to be secreted in association with exosomes and has been also shown to be present on the surface of HIV-infected cells. Nef-expressing cells have a dramatically altered subcellular morphology and have been shown to induce the intracellular accumulation of multivesicular bodies and the extracellular accumulation of exosomes. Exosomes have been postulated to play a role in the production of HIV-1 virions. The so called "Trojan Exosome" hypothesis suggests that HIV-1 particles can "piggyback" on the process of exosome biogenesis to provide a means of transfer of infectious particles from one cell to another (Izquierdo-Useros et al., *PLoS pathogens,* 6(3):1-9, 2010). Although some of the aspects of this theory have been questioned, the research has established a precedent for HIV-1 proteins being carried out of the cell and from one cell to another via the exosome network.

There is great interest in exploiting the properties of exosomes for diagnostic, vaccination, and therapeutic applications, including new and effective methods for preparing recombinant proteins at an industrial scale, for vaccine preparation, and for immunotherapy. The present invention provides compositions and methods for exosomal expression of recombinant proteins.

SUMMARY

One aspect of the present application relates to a method for preparing a protein composition. The method comprises the steps of culturing an exosome-producing cell expressing a Nef-fusion protein comprising a Nef-derived peptide fused to a protein of interest; isolating exosomes from the exosome-producing cell culture; and purifying the protein of interest from the isolated exosomes.

Another aspect of the present application relates to a method for delivering a protein of interest to a target cell in a mammal. The method comprises administering to the mammal an exosome comprising a Nef-fusion protein comprising a Nef-derived peptide fused to the protein of interest.

Another aspect of the present application relates to a method for inducing an immune response in a mammal. The method comprises administering to a mammal an exosome comprising a Nef-fusion protein comprising a Nef-derived peptide fused to an immunogenic protein of interest.

Another aspect of the present application relates to a method for detecting a target molecule in a sample. The method comprises contacting a sample from a subject with a Nef-fusion protein that binds specifically to the target molecule, detecting a binding of the target molecule in the sample to the Nef-fusion protein, and determining a level of the target molecule in the sample, wherein a medical condition is indicated if the level of the target molecule is outside a reference range.

Another aspect of the present application relates to a pharmaceutical composition, comprising an exosome comprising a Nef-fusion protein containing a Nef-derived peptide fused to a protein of interest, and a pharmaceutically acceptable carrier.

Another aspect of the present application relates to a Nef-fusion protein produced by culturing cells that produce exosomes containing the Nef-fusion protein; isolating exosomes from the exosome-producing cell culture; and purifying the Nef-fusion protein from the isolated exosomes, wherein the Nef-fusion protein comprises a Nef-derived peptide fused to a protein of interest.

BRIEF DESCRIPTION OF THE DRAWINGS

FIGS. 1A-C show co-expression of Nef with exosomal markers acetylcholinesterase (AChE) and CD45 release from untransfected and Nef-GFP-transfected Jurkat cells. In FIG. 1A, $1\times10^6$ Jurkat cells were mock-transfected or HIV-1 wtNef-GFP for 48 h at 37° C. Cell lysates prepared therefrom were examined for HIV-1 Nef, AChE, CD45, and tubulin expression by Western analysis. Columns: UT, untransfected Jurkat cell lysates; Nef, HIV-1 wtNef-GFP-transfected cell lysates. Rows: Probed with: Nef, HIV-1 Nef monoclonal antibody; AChE, AChE antibody; CD45, CD45 antibody; tubulin, tubulin antibody. In FIG. 1B, differential centrifugal high-molecular-weight pellets were examined for HIV-1 Nef, AChE, and CD45 by Western analysis. Columns: lane 1, 10,000×g pellet; lane 2, 50,000×g pellet;

lane 3, 100,000×g pellet; lane 4, 400,000×g pellet; lane 5, 400,000×g spent supernatant. Rows: top two panel set: untransfected Jurkat culture pellet examined with AChE or CD45 antibodies; lower three panel set: HIV-1 Nef-GFP-transfected Jurkat culture pellet examined with HIV-1 Nef monoclonal, AChE, or CD45 antibodies. FIG. 1C shows densitometric analysis of the Western data (NIH Image J software analysis) in FIGS. 1A and 1B. AChE and CD45 band densities from untransfected cells and AChE, CD45, and Nef band densities from HIV-1 Nef-transfected cells were normalized against intracellular tubulin, and to report combined 100,000×g plus 400,000×g band density units per $1\times10^6$ cells. This is the combined data from multiple experiments and the data were analyzed using Student's t-test comparing untransfected values and wtNef-GFP-transfected values and displaying the p-values where $p<0.05$ is significant. Transfection efficiencies for these experiments were 85%±2%.

FIG. 2A shows representative images from one experiment: Cell lysate (lane 1); culture media (supernatant; lane 2); 50,000×g pellet (lane 3); 400,000×g pellet (Diff. Cent.; lane 4); Gradient fractions 4-11 (lanes 5-12). Gradient fractions 1, 2, 3, and 12, which had no protein in them, are not shown. FIG. 2B shows data collated from multiple experiments. Bands visualized on Western blots were measured by densitometry. Data were analyzed using Student's t-test comparing Alix from untransfected cell cultures and wtNef-GFP-transfected cell cultures, with p values<0.01 being scored as significant.

FIG. 4A shows various Nef deletion mutants, including Nef: NefΔ31-206 containing aa residues 1-30; NefΔ1-12 containing aa 13-70 but lacking the myristoylation site G2 and the K4K7 basic region; NefΔ1-40 containing aa 41-70; NefΔ51-206 containing aa 1-50; NefΔ65-206 containing aa 1-65; NefΔ71-206 containing aa 1-70; NefΔ91-206 containing aa 1-90; and NefΔ150-206 containing aa 1-150; NefΔ200-206 containing aa 1-200. FIG. 4B shows various amino acid replacement mutants, including Nef4R(17-22)/4A, in which R17, R19, R21, and R22 are replaced with four alanines; NefK39P, in which K39 is replaced with a proline to disrupt the helix; SS45,46AA, in which S45 and S46 are replaced with two alanines; P25A, in which P25 is replaced with an alanine; 29GVG31/3A, in which G29, V30, and G31 are replaced with three alanines; T44A, in which T44 is replaced with an alanine; $Nef^{62}EEEE^{65}/4A$ (PACS), in which E62-65 are replaced with five alanines; $NefSMR/^{66}VGFPV^{70}/5A$, in which V66, G67, F68, P69, and V70 are replaced with five alanines (in wt as well as Nef13-70 background); $SMR/^{66}AGFPV^{70}$, in which V66 is replaced with an alanine; $SMR/^{66}VAFPV^{70}$, in which F68 is replaced with an alanine; $SMR/^{66}VGFAV^{70}$, in which P69 is replaced with an alanine; and $SMR^{66}VGFPA^{70}$, in which V70 is replaced with an alanine.

FIG. 5A shows the sequence of HIV-1 Nef showing structural domains required for cellular interactions, including the basic amino acid 1 and 2 motifs (BAA-1, BAA-2), helix-1 and helix-2, membrane targeting domain, PACS, and SMR motifs. FIG. 5B shows the sequence of SIV Nef showing structural domains required for cellular interactions.

FIG. 6A shows truncation mutagenesis to determine Nef secretion sequences. The relative fluorescence of carboxy-terminal deletion mutants of Nef compared to the wtNef-GFP is shown. Media were collected and assayed from the 48-h-old cultures of HEK293 cells transfected with the wt, NefΔ31-206 (1-30), NefΔ51-206 (1-50), NefΔ66-206 (1-65), NefΔ71-206 (1-70), NefΔ91-206 (1-90), NefΔ151-206 (1-150), NefΔ201-206 (1-200), NefΔ1-12 (13-206), NefΔ1-12 and Δ71-206 (13-70), NefΔ1-40 and Δ71-206 (41-70), and untransfected HEK293 cells (bar 12). FIG. 6B shows replacement mutagenesis to fine map Nef secretion sequences. The relative fluorescence of N-terminal replacement mutants of Nef in the 1-70 aa region and compared to the wtNef-GFP is shown. Media were collected and assayed from the 48-h cultures of HEK293 cells transfected with wtNef, NefΔ71-206 (1-70), NefG2A, NefK4K7, Nef K39P, $Nef^{39}K/P$, $Nef^{45,46}S/2A$, NefP25A, $Nef^{29}GVG^{31}/3A$, NefT44A, $Nef^{66}VGFPV^{79}/5A$, $Nef^{62}EEEE^{65}/4A$ (PACS), $Nef^{17,19,21,22}R/4A$, and untransfected HEK293 cells. FIG. 6C shows a newly identified domain on HIV-1 Nef. The relative fluorescence of N-terminal deletion and replacement mutants of Nef in the 66-70 aa region compared to the wtNef is shown. Media were collected and assayed from the 48-h cultures of HEK293 cells transfected with wtNef, GFP, $Nef^{66}AGFPV^{70}$, $Nef^{66}VAFPV^{70}$, $Nef^{66}VGAPV^{70}$, $Nef^{66}VGFAV^{70}$, $Nef^{66}VGFPA^{70}$, and untransfected HEK293 cells. FIGS. 6D-F show the Nef-induced secretion domains function similarly in multiple cell types. Jurkat cells ($1\times10^6$) transfected with HIV-1 wtNef (bar 1), NefΔ71-206 (bar 2), NefΔ1-12 and Δ71-206 (bar 3), NefΔ1-12 (bar 4), $Nef^{17,19,21,22}R/4A$ (bar 5), $Nef^{62}EEE^{65}/4A$ (PACS, bar 6), $Nef^{66}AGFPV^{70}$ (SMR, bar 7), GFP (bar 8), and untransfected cells (bar 9) (FIG. 6D), THP-1 (FIG. 6E), and U937 (FIG. 6F) monocytes by Gene Pulser Xcell Electroporation System (Bio-Rad Laboratories, Inc., CA). Cells were incubated in RPMI 1640 medium for 48 h at 37° C. and removed from the culture supernatant by centrifugation at 2000×g for 5 min. In all experiments, the error bars show the standard errors of the measurements. Transfection efficiencies for Jurkat cells (80-86.67%), for THP-1 cells (60-65%), and for U937 cells (55-60%). These results are a compilation of at least three independent experiments.

FIG. 7 shows an alignment of the PACS/SMR regions of HIV-1 Nef. Amino acid consensus sequences for 13 HIV-1 subtypes were determined as described in Materials and Methods. The PACS-SMR consensus sequences were then aligned to illustrate the degree of homology in these required secretion domains of Nef. Dashes (—) indicate gaps inserted to facilitate the alignment.

In FIG. 8A, HEK293 cells were transfected with HIV-1 Nef-GFP mutants and stained by PI. Columns: bar 1, mock, untransfected HEK293 cells; bar 2, pQBI-GFP, transfected pQBI-GFP; bar 3, wtNef-GFP(1-206), transfected HIV-1 wtNef-GFP; bar 4, wtNef-GFP (1-70), transfected NefΔ71-206; bar 5, wtNef-GFP (13-70), transfected NefΔ1-12 and Δ71-206; bar 6, Nef-4R4A-GFP (1-206), transfected $Nef^{17,19,21,22}R/4A$; bar 7, Nef-PACS-GFP (1-206), transfected $Nef^{62}EEEE^{65}/4A$; bar 8, Nef-AGFPV-GFP (1-206), transfected $Nef^{66}AGFPV^{70}$. In FIG. 8B, HEK293 cells were transfected with HIV-1 Nef at 37° C. for 48 h and then cells were assayed by TUNEL. Columns: bar 1, pQBI-RFP, transfected pQBI-RFP in HEK293 cells; bar 2, HIV-1 wtNef-RFP, transfected HIV-1 wtNef-RFP.

In FIG. 9A, cell lysates and vesicles collected from each condition were examined for histones through Coomassie brilliant blue staining of PAGE gels. Lanes 1,3,5, and 7 are cell lysates from each condition; lanes 2, 4, 6, and 8 are pellets from cell lysates spun at 130,000×g. Lanes 1 and 2 are from cells treated with 10 μM camptothecin; lanes 3 and 4 are from cells transfected with HIV-1 wtNef; lanes 5 and 6 are from cells transfected with $Nef^{66}AGFPV^{70}$; lanes 7 and 8 are from untransfected cells. His denotes the region of the gel containing the histone bands. In FIG. 9B, cell lysates and vesicles were analyzed by Western analysis for the presence of histones (top panel set, histone antibody), GFP (middle panel set, GFP antibody), and HIV-1 Nef (bottom panel set, Nef polyclonal antibody). Lane 1, cell lysates; lane 2, 300×g pellet; lane 3, 1200×g pellet; lane 4, 10,000×g pellet; lane 5, 130,000×g pellet. Individual panels of each panel set: top panel, Camp, cells were treated with 10 μM camptothecin; second panel, Nef, HIV-1 wtNef-GFP-transfected cells; third panel, Nef-SMR (HIV-1 $Nef\text{-}^{66}VGFPV^{70}/5A$-GFP)-transfected cells; bottom panel, UT, untransfected cells.

In FIGS. 10A-10C, $1\times10^6$ HEK293 cells were transfected with 1 μg of HIV-1 wtNef-GFP for 48 h and then followed by Western analysis of HEK293 cell lysates from wtNef or mutant transfections. Cell cultures were transfected with pQBI-Nef-GFP (NefGFP; lane 1), pQBI-GFP (GFP; lane 2), pQBI-$Nef^{62}EEEE^{65}/4AGFP$ (PACS replacement; lane 3), pQBI-$Nef^{66}AGFPV^{70}GFP$ (SMR replacement lane 4), pQBI-$Nef^{17,19,21,22}/R4AGFP$ (BAA-2 replacement; lane 5), or untransfected HEK293 cells (UT; lane 6). Cell lysates were collected and analyzed by SDS-PAGE followed by Western analysis probing with anti-GFP antiserum. Representative images of several independent experiments are shown. The relative positions of Nef-GFP and Nef-GFP deletion mutants' cellular protein that hybridizes to the anti-GFP antiserum are indicated. FIG. 10D shows densitometry was performed and the readings from multiple independent analyses are displayed as the average densitometric units for any particular assay with standard error of measurement displayed.

DETAILED DESCRIPTION

Figures 2A, 2B:
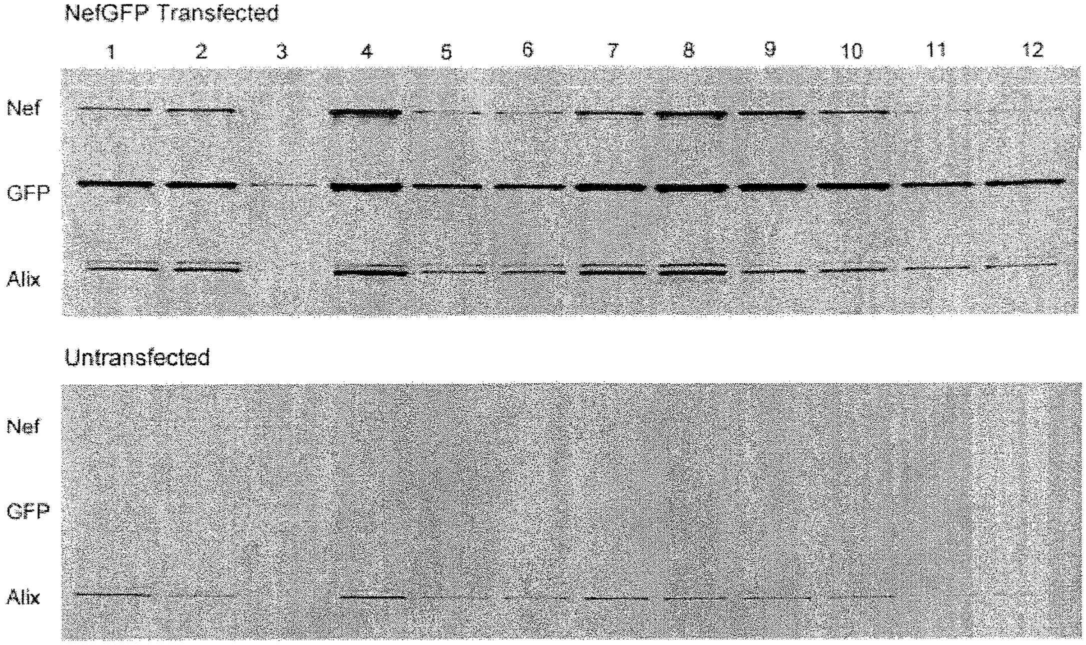
FIGS. 2A-B show an analysis of the vesicular nature of secreted Nef protein. Cells and conditioned media were collected from untransfected or wtNef-GFP-transfected Jurkat cultures. Culture media were processed via differential centrifugation, with spins at 1200×g, 10,000×g, 50,000×g, 200,000×g, and 400,000×g. Both 200,000×g and 400,000×g pellets were subjected to sucrose gradient flotation. Cell lysates, culture medium, 50,000×g pellets and 400,000×g pellets and flotation gradient fractions were examined by Western blotting for Nef, GFP, and Alix.
Figure 3:
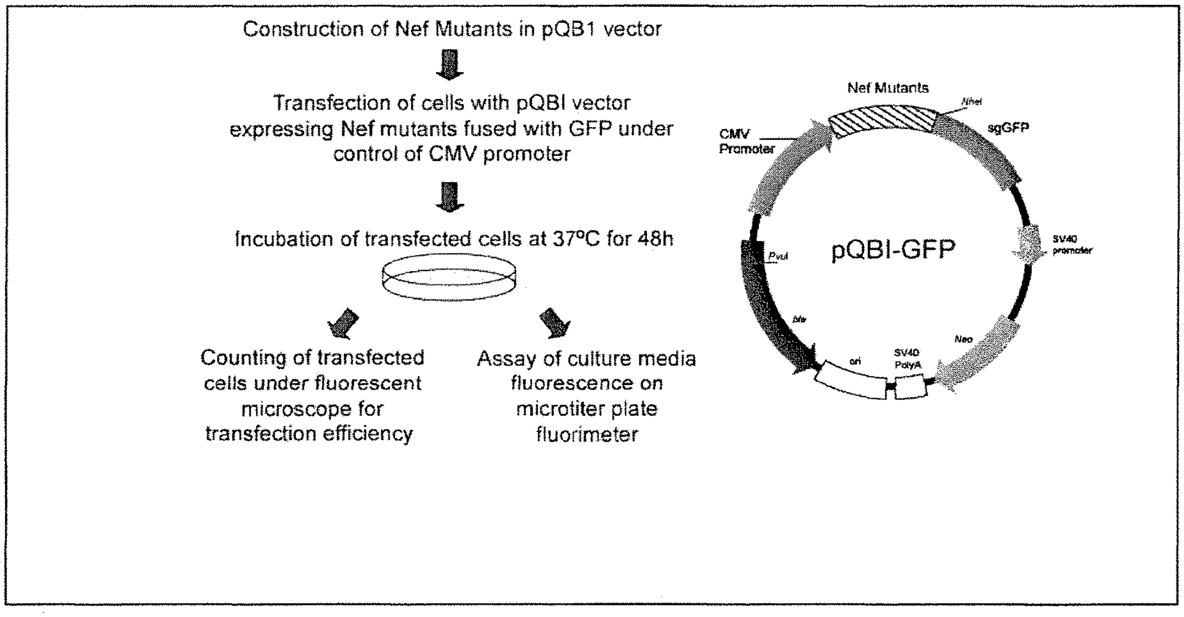
FIG. 3 shows a transient transfection strategy for identifying the Nef structural requirements for exosome secretion.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

Method of Producing Nef-Fusion Protein

One aspect of the present application relates to a method for producing a protein composition comprising culturing an exosome-producing cell expressing a Nef-fusion protein comprising a Nef-derived peptide fused to a protein of interest; isolating exosomes from the exosome-producing cell culture; and purifying the Nef-fusion protein or the protein of interest from the isolated exosomes.

As used herein, the term "Nef-derived peptide" refers to the full length HIV Nef peptide (SEQ ID NO:1), the full length SIV Nef peptide (SEQ ID NO:2), a fragment of the full length HIV Nef peptide that comprises amino acid residues 13-41 of SEQ ID NO:1 (i.e., SEQ ID NO:3), a fragment of the full length SIV Nef peptide that comprises amino acid residues 1-102 of SEQ ID NO:2 (i.e., SEQ ID NO:4), or variants thereof. A variant of the full length Nef peptide or the Nef fragment includes peptides that share at least 95%, 96%, 97%, 98% or 99% homology to the full length Nef peptide or the Nef fragment, as well as peptides that contain one or more substitutions, additions and/or deletions that do not significantly alter the bioactivity of the full length Nef peptide or the Nef fragment. In some embodiments, the Nef-derived peptide is a Nef fragment comprising SEQ ID NO:3 or a variant the HIV Nef fragment. In some other embodiments, the Nef-derived peptide is a Nef fragment comprising amino acid residues 13-70 of SEQ ID NO:1 (SEQ ID NO:5) or a variant the Nef fragment. In some other embodiments, the Nef-derived peptide is a Nef fragment comprising amino acid residues 1-70 of SEQ ID NO:1 (SEQ ID NO:6) or a variant the Nef fragment. In some embodiments, the Nef-derived peptide is a Nef fragment comprising SEQ ID NO:4 or a variant the Nef fragment. In certain embodiments, the Nef-derived peptide has a length of 30-70, 60-70, 70-150, 150-206, 30-102, 102-180 and 180-263 amino acids.

The Nef-Fusion Protein

The Nef-fusion protein comprises a Nef-derived peptide fused to a protein of interest. In some embodiments, the Nef-fusion protein further comprises one or more additional amino acid sequences encoding one or more functional domains. Exemplary functional domains include, but are not limited to, affinity tags, protease cleavage sites, targeting domains, reporters, enzymes, or combination thereof.

In certain embodiments, an affinity tag may be included to facilitate purification of the Nef-fusion protein and/or protein of interest by affinity chromatography. The affinity tag may include affinity tag known to those of skill in the art, including, but not limited to, glutathione S-transferase (GST), Histidine tag (e.g., 6× His), maltose binding protein (MBP), Protein A, thioredoxin, ubiquitin, biotin, calmodulin binding peptide (CBP), streptavidin tag, and various immunogenic peptide tags, including FLAG octapeptide tag, hemaglutinin A (HA) tag, myc tag, and the like.

In some embodiments, proteolytic cleavage sites may be engineered into the Nef-fusion protein to promote the release of the protein of interest from Nef and/or other peptide functional domains, including affinity tags, in conjunction with fusion protein synthesis or purification. Exemplary protease cleavage sites include, but are not limited to, cleavage sites sensitive to thrombin, furin, factor Xa, metalloproteases, enterokinases, and cathepsin.

The targeting domain may comprise amino acid sequences conferring cell-type specific or cell differentiation-specific targeting. The targeting domain may be incorporated into the Nef-fusion protein or it can be fused to a coexpressed membrane-bound exosomal marker protein. Preferably the targeting domain is fused to an extracellular domain in the membrane-bound protein. The targeting domain may comprise an antibody or antibody derivative, a peptide ligand, a receptor ligand, a receptor fragment, a hormone, etc. Exemplary membrane-bound exosomal marker proteins include, but are not limited to tetraspanins, such as CD9, CD63, CD81, CD82, and CD151, and a variety of GPI (glycerol-phosphatidyl inositol)-anchored proteins, among others.

Exemplary antibody or antibody derived targeting domains may include any member of the group consisting of: IgG, antibody variable region; isolated CDR region; single chain Fv molecule (scFv) comprising a VH and VL domain linked by a peptide linker allowing for association between the two domains to form an antigen binding site; bispecific scFv dimer; minibody comprising a scFv joined to a CH3 domain, single chain diabody fragment, dAb fragment, which consists of a VH or a VL domain; Fab fragment consisting of VL, VH, CL and CH1 domains; Fab' fragment, which differs from a Fab fragment by the addition of a few residues at the carboxyl terminus of the heavy chain CH1 domain, including one or more cysteines from the antibody hinge region; Fab'-SH fragment, which is a Fab' fragment in which the cysteine residue(s) of the constant domains bear a free thiol group; $F(ab')_2$, bivalent fragment comprising two linked Fab fragments; Fd fragment consisting of VH and CH1 domains; derivatives thereof, and any other antibody fragment(s) retaining antigen-binding function. Fv, scFv, or diabody molecules may be stabilized by the incorporation of disulphide bridges linking the VH and VL domains. When using antibody-derived targeting agents, any or all of the targeting domains therein and/or Fc regions may be "humanized" using methodologies well known to those of skill in the art.

In some embodiments, the targeting domain comprises an antibody-derived or peptide-derived targeting domain from a phage display library. Phage display libraries engineered for binding cell surface molecules or receptors are well known to those of skill in the art.

Functional domains in the Nef-fusion proteins of the present invention may be separated from one another by a spacer or linker to facilitate the independent folding of each peptide portion relative to one another and ensure that the individual peptide portions in a fusion protein do not interfere with one another. The spacer may include any amino acid or mixtures thereof. In one embodiment, the spacer comprises between 1 to 50 amino acids, preferably 3 to 15 amino acids in length. Preferably, a chosen spacer will increase the flexibility of the protein and facilitate adoption of an extended conformation. Preferred peptide spacers are comprised of the amino acids proline, lysine, glycine, alanine, and serine, and combinations thereof. In one embodiment, the linker is a glycine rich linker. In a particular embodiment, the spacer having the formula $[(Gly)_n\text{-Ser/Ala}]_m$ (SEQ ID NO:7) where n is from 1 to 4, inclusive, and m is from 1 to 4, inclusive.

The Exosome-Producing Cell

The exosome-producing cell can be any cell capable of producing exosomes. In some embodiments, the exosome-producing cell is a cell of mammalian origin. In other embodiments, the exosome-producing cell is a human cell. The exosome-producing cell produces and secretes membrane vesicles of endosomal origin by fusion of late endosomal multivesicular bodies with the plasma membrane. Cells from various tissue types have been shown to secrete exosomes, such as dendritic cells, B lymphocytes, tumor cells, T lymphocytes and mast cells, for instance. Preferred exosome-producing cells include mammalian tumor cells, mammalian B and T lymphocytes, and mammalian dendritic cells, typically of murine or human origin. In this regard, the cells are preferably immortalized dendritic cells, immature dendritic cells or tumor cells. Furthermore, for the production of antibody, it may be advantageous to use B lymphocytes as exosome-producing cells, since the resulting exosomes comprise accessory functions and molecules such as MHC class II molecules that facilitate antibody production. Furthermore, it has been shown that B cells-derived exosomes are able to bind to follicular dendritic cells, which is another important feature for antibody induction.

In some embodiments, the exosome-producing cell is stably transformed with a vector expressing the Nef-fusion protein. In other embodiments, the exosome-producing cell is transiently transfected with a vector expressing the fusion protein.

Any suitable expression vector may be used to introduce and express Nef-fusion proteins. As used herein, the term "expression vector" includes any nucleic acid capable of expressing the fusion protein in vivo. Expression vectors may be delivered to cells using two primary delivery schemes: viral-based delivery systems using viral vectors and non-viral based delivery systems using, for example, plasmid vectors. Such methods are well known in the art and readily adaptable for use with the compositions and methods described herein. In certain cases, these methods can be used to target certain diseases and cell populations by using the targeting characteristics inherent to the carrier or engineered into the carrier.

The expression vector contains one or more transcriptional regulatory elements, including promoters and/or enhancers, for directing the expression of Nef-fusion proteins. A promoter comprises a DNA sequence that functions to initiate transcription from a relatively fixed location in regard to the transcription start site. A promoter contains core elements required for basic interaction of RNA polymerase and transcription factors, and may operate in conjunction with other upstream elements and response elements.

As used herein, the term "promoter" is to be taken in its broadest context and includes transcriptional regulatory elements (TREs) from genomic genes or chimeric TREs therefrom, including the TATA box or initiator element for accurate transcription initiation, with or without additional TREs (i.e., upstream activating sequences, transcription factor binding sites, enhancers, and silencers) which regulate activation or repression of genes operably linked thereto in response to developmental and/or external stimuli, and trans-acting regulatory proteins or nucleic acids. The promoter may be constitutively active or it may be active in one or more tissues or cell types in a developmentally regulated manner. A promoter may contain a genomic fragment or it may contain a chimera of one or more TREs combined together.

Preferred promoters are those capable of directing expression in a target cell of interest. The promoters may include constitutive promoters (e.g., HCMV, SV40, elongation factor-1α (EF-1α)) or those exhibiting preferential expression in a particular cell type of interest. Enhancers generally refer to DNA sequences that function away from the transcription start site and can be either 5' or 3' to the transcription unit. Furthermore, enhancers can be within an intron as well as within the coding sequence. They are usually between 10 and 300 bp in length, and they function in cis. Enhancers function to increase and/or regulate transcription from nearby promoters. Preferred enhancers are those directing high-level expression in the exosome expressing cell.

The promoter and/or enhancer may be specifically activated either by light or specific chemical inducing agents. In some embodiments, inducible expression systems regulated by administration of tetracycline or dexamethasone, for example, may be used. In other embodiments, gene expression may be enhanced by exposure to radiation, including gamma irradiation and external beam radiotherapy (EBRT), or alkylating chemotherapeutic drugs.

Cell or tissue-specific transcriptional regulatory elements (TREs) can be incorporated into expression vectors to allow for transcriptional targeting of expression to desired cell types. Expression vectors generally contain sequences for transcriptional termination, and may additionally contain one or more elements positively affecting mRNA stability. An expression vector may further include an internal ribosome entry site (IRES) between adjacent protein coding regions to facilitate expression two or more proteins from a common mRNA in an infected or transfected cell. Additionally, the expression vectors may further include nucleic acid sequence encoding a marker product. This marker product is used to determine if the gene has been delivered to the cell and once delivered is being expressed. Preferred marker genes are the *E. coli* lacZ gene, which encodes ß-galactosidase, and green fluorescent protein.

The expression vector can be introduced into the exosome-producing cells by any conventional method, such as by naked DNA technique, cationic lipid-mediated transfection, polymer-mediated transfection, peptide-mediated transfection, virus-mediated infection, physical or chemical agents or treatments, electroporation, etc. In one embodiment, cells transfected with the vector may be used directly as a source of exosomes (transient transfection). Alternatively, cells may be transfected with a vector expressing a Nef-fusion protein along with a selectable marker facilitating selection of stably transformed clones expressing the fusion protein. The exosomes produced by such cells may be collected and/or purified according to techniques known in the art, such as by centrifugation, chromatography, etc. as further described in the cited references and Examples herein.

Examples of suitable selectable markers for mammalian cells include dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, mycophenolic acid, or hygromycin. The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

In some embodiments, the Nef-fusion proteins are delivered from viral-derived expression vectors. Exemplary viral vectors may include or be derived from adenovirus, adeno-associated virus, herpesvirus, vaccinia virus, poliovirus, poxvirus, HIV virus, lentivirus, retrovirus, Sindbis and other RNA viruses, and the like. Also preferred are any viral families which share the properties of these viruses which make them suitable for use as vectors. Retroviruses include Murine Moloney Leukemia virus (MMLV), HIV and other lentivirus vectors. Adenovirus vectors are relatively stable and easy to work with, have high titers, and can be delivered in aerosol formulation, and can transfect non-dividing cells. Poxviral vectors are large and have several sites for inserting genes, they are thermostable and can be stored at room temperature. Viral delivery systems typically utilize viral vectors having one or more genes removed and with and an exogenous gene and/or gene/promoter cassette being inserted into the viral genome in place of the removed viral DNA. The necessary functions of the removed gene(s) may be supplied by cell lines which have been engineered to express the gene products of the early genes in trans.

Exemplary exosome-producing cells include human Jurkat, human embryonic kidney (HEK) 293, Chinese hamster ovary (CHO) cells, mouse WEHI fibrosarcoma cells, and unicellular protozoan species, such as *Leishmania tarentolae*. In addition, stably transformed, exosome-producing cell lines may be produced using primary cells immortalized with c-myc or other immortalizing agents. In some embodiments, the cell lines expresses at least 1 mg, at least 2 mg, at least 5 mg, at least 10 mg, at least 20 mg, at least 50 mg, or at least 100 mg of the Nef-fusion protein/liter of culture.

In one embodiment, the cell line comprises a stably transformed *Leishmania* cell line, such as *Leishmania tarentolae*. *Leishmania* are known to, secrete exosomes and are known to provide a robust, fast-growing unicellular host for high level expression of eukaryotic proteins exhibiting mammalian-type glycosylation patterns. A commercially available *Leishmania* eukaryotic expression kit is available (Jena Bioscience GmbH, Jena, Germany).

Isolation of Exosomes and Purification of Nef-Fusion Protein

Exosomes are isolated from exosome-producing cells. Exosome-producing cells are cultured and maintained in any appropriate culture medium, such as RPMI, DMEM, and AIM V®. The culture medium is preferably a protein-free medium so as to avoid contamination of exosomes by media-derived proteins. In some embodiments, exosomes are isolated from the culture supernatants by sequential centrifugation. The Nef-fusion proteins are then purified using conventional protein purification methodologies (e.g., affinity purification, chromatography, etc) known to those of skill in the art. In certain embodiments, the purified Nef-fusion protein is treated to release the protein of interest from the Nef-derived peptide. The protein of interest is then purified from the treated Nef-fusion protein using conventional protein purification methodologies.

In some other embodiments, the isolated exosomes are treated to release the protein of interest from the Nef-derived peptide. The protein of interest is then purified from the treated exosomes using conventional protein purification methodologies. Therefore, one aspect of the present application relates to a Nef-fusion protein produced by culturing cells that produce exosomes containing the Nef-fusion protein; isolating exosomes from the exosome-producing cell culture; and purifying the Nef-fusion protein from the isolated exosomes, wherein the Nef-fusion protein comprises a Nef-derived peptide fused to a protein of interest.

Methods of Using the Nef-Fusion Protein and Exosomes Containing the Nef-Fusion Protein Another aspect of the present application relates to a method of treating cancer in a subject. In certain embodiments, the method includes the step of administering to a subject in need of such treatment, an effective amount of an exosome comprising the Nef-fusion protein described above, wherein the protein of interest is a cancer-specific antigen and wherein the exosome is isolated from a professional antigen presenting cell, such a B lymphocyte or a dendritic cell.

In other embodiments, exosomes containing the Nef-fusion protein are further loaded with one or more immunogenic agents, including antigens, peptides, small molecule drugs and/or nucleic acids, such as siRNAs. Such agents may be loaded into exosomes using conventional delivery methodologies, employing, for example, transfection agents, including liposomal and peptide-based transfection agents, electroporation, microinjection and the like.

In certain embodiments, exosomes containing the Nef-fusion protein are loaded with an siRNA targeting a cancer marker that is over-expressed in cancer cells. In one embodiment, purified exosomes are loaded with exogenous siRNA by electroporation. The exosomes may be further modified to target specific organ, tissue or cells.

Another aspect of the present application relates to a method for inducing an immune response in a mammal. The method comprises administering to a mammal an exosome containing a Nef-fusion protein comprising an immunogenic protein of interest, wherein the exosome composition is sufficient to induce an immune response in the mammal. The exosome may be introduced into the mammal as a vaccine, an immunotherapeutic composition for treating a disease, or an immunogen for raising antibodies in an animal.

In one embodiment, the exosome is administered as a vaccine. In another embodiment, the exosome is administered as an immunotherapeutic composition, such as an immunosuppressive exosome. In another embodiment, the Nef-fusion protein comprises a Nef-derived fragment fused to an immunogenic protein from a bacterium, virus, fungus, or protozoan. In a further embodiment, the exosome is isolated from an antigen presenting cell, such as a dendritic cell, B lymphocyte, or macrophage.

Another aspect of the present application relates to immunoassay methods, compositions or devices using the Nef-fusion protein produced by the method of the present application. In some embodiments, the method is a detection method comprising the steps of contacting a sample from a subject with a Nef-fusion protein that binds specifically to a target molecule, detecting a binding of the target molecule in the sample to the Nef-fusion protein, and determining a level of the target molecule in the sample, wherein a medical condition is indicated if the level of the target molecule is outside a reference range.

The sample can be a cell sample, tissue sample or body fluid sample, such as a blood sample or a urine sample.

In some embodiments, the Nef-fusion protein is attached to a solid support to capture an antibody of interest or an antigen of interest from a sample. By "solid support" is meant a non-aqueous matrix to which the Nef-fusion protein of the present invention can adhere or attach. Examples of solid phases encompassed herein include those formed partially or entirely of glass (e.g., controlled pore glass), polysaccharides (e.g., agarose), polyacrylamides, silicones, and plastics such as polystyrene, polypropylene and polyvinyl alcohol. The solid support can be in the form of tubes, microtiter plates, beads, or cells.

Examples of immunoassays include enzyme-linked immunosorbent assay (ELISA), radioimmunoassay (RIA), flow cytometry, protein array, microbead assay, magnetic capture, and combinations thereof. The medical condition can comprise any disease state in which the presence of a target antigen and/or an antibody against the target antigen in the subject is indicative of the medical condition, such as a cancerous conditions, a microbial infection etc.

In one embodiment, the exosome is conjugated to a solid support. In some embodiments, exosome coated assay plates or wells are contacted with serum from a patient and tested for the presence or absence of antibodies binding to the Nef-fusion protein comprising a target antigen or marker diagnostic for a medical condition. As the antigen concentration increases in the plates or wells the amount of antibody increases leading to a higher measured response. Typically an enzyme is attached to the secondary antibody which must be generated in a different species than primary antibodies (i.e., if the primary antibody is a rabbit antibody than the secondary antibody would be an anti-rabbit from goat, chicken, etc., but not rabbit). The substrate for the enzyme is added to the reaction that forms a colorimetric readout as the detection signal. The signal generated is proportional to the amount of target antigen present in the sample.

The antibody linked reporter used to measure the binding event determines the detection mode. A spectrophotometric plate reader may be used for colorimetric detection. Several types of reporters have been recently developed in order to increase sensitivity in an immunoassay. For example, chemiluminescent substrates have been developed which further amplify the signal and can be read on a luminescent plate reader. Also, a fluorescent readout where the enzyme step of the assay is replaced with a fluorophor tagged antibody is becoming quite popular. This readout is then measured using a fluorescent plate reader.

In some embodiments, a competitive binding assay based on the competition of labeled and unlabeled ligand for a limited number of antibody binding sites may be used. Competitive inhibition assays are often used to measure small analytes. Only one antibody is used in a competitive binding ELISA. This is due to the steric hindrance that occurs if two antibodies would attempt to bind to a very small molecule. A fixed amount of labeled ligand (tracer) and a variable amount of unlabeled ligand are incubated with the antibody. According to law of mass action, the amount of labeled ligand is a function of the total concentration of labeled and unlabeled ligand. As the concentration of unlabeled ligand is increased, less labeled ligand can bind to the antibody and the measured response decreases. Thus the lower the signal, the more unlabeled analyte there is in the sample. The standard curve of a competitive binding assay has a negative slope.

In certain other embodiments, a detection marker may be detected using exosome or Nef-fusion protein coated microbeads. In some embodiments, the microbeads are magnetic beads. In other embodiments, the beads are internally color-coded with fluorescent dyes and the surface of the bead is tagged with an exosome expressing a fusion protein of interest that can bind an antibody in a test sample. Antibody-bound exosomes may be directly labeled with a fluorescent tag or indirectly labeled with an anti-marker antibody conjugated to a fluorescent tag and may contain two sources of color, one from the bead and the other from the fluorescent tag. The beads can then pass through a laser and, on the basis of their color (and/or size), either get sorted or measured for color intensity, which is processed into quantitative data for each reaction.

Compositions Containing the Nef-Fusion Protein

A further aspect of the present application relates to compositions for treating a disease condition in accordance with the methods described herein. In one embodiment, the composition comprises a Nef-fusion protein containing a Nef-derived peptide fused to a protein of interest and a pharmaceutically acceptable carrier. In another embodiment, the composition comprises an exosome comprising a Nef-fusion protein containing a Nef-derived peptide fused to a protein of interest as described above and a pharmaceutically acceptable carrier.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

In another embodiments, the composition comprises a Nef-fusion protein containing exosome further loaded with one or more immunogenic agents, including antigens, peptides, small molecule drugs, and nucleic acids, such as siRNAs. Such agents may be loaded into exosomes as described above.

In other embodiments, the composition comprises an expression vector configured to express the fusion protein so as to redirect its localization to secreted exosomes.

Pharmaceutical carriers are known to those skilled in the art. These most typically would be standard carriers for administration of drugs to humans, including solutions such as sterile water, saline, Ringer's solution, dextrose solution, and buffered solutions at physiological pH. Typically, an appropriate amount of a pharmaceutically-acceptable salt is used in the formulation to render the formulation isotonic. The pH of the solution is preferably from about 5 to about 8, and more preferably from about 7 to about 7.5. It will be apparent to those skilled in the art that certain carriers may be more preferable depending upon, for instance, the route of administration and exosome concentration being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Compositions for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The exosome materials may be targeted to a particular cell type via targeting domains as described above. The targeting domain may be incorporated into the Nef-fusion protein or in another coexpressed exosome protein as described above.

The pharmaceutical compositions described herein can be packaged together in a suitable combination as a kit useful for performing, or aiding in the performance of, the disclosed method.

The pharmaceutical composition disclosed herein may be administered in a number of ways depending on whether local or systemic treatment is desired, and on the area to be treated. For example, the compositions may be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the pharmaceutical composition into the nose and nasal passages through one or both of the nares and can comprise delivery by a spraying mechanism or droplet mechanism, or through aerosolization of the pharmaceutical composition. Administration of the composition by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained.

The exact amount of the compositions required will vary from subject to subject, depending on the species, age, weight and general condition of the subject, the particular nucleic acid or vector used, its mode of administration and the like. An appropriate amount can be determined by one of ordinary skill in the art using only routine experimentation given the teachings herein. Thus, effective dosages and schedules for administering the compositions may be determined empirically, and making such determinations is within the skill in the art. The dosage ranges for the administration of the compositions are those large enough to produce the desired effect in which the symptoms of the disorders are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of the disclosed composition used alone might range from about 1 μg/kg to up to 100 mg/kg of body weight or more per day, depending on the factors mentioned above.

The present invention is further illustrated by the following examples which should not be construed as limiting. The contents of all references, patents and published patent applications cited throughout this application, as well as the Figures and Tables are incorporated herein by reference.

EXAMPLE 1

Characterization of HIV Type 1 Nef-Induced Exosome Secretion

Within the N-terminal 70 amino acids of HIV-1 Nef several domains were identified as important for Nef-induced vesicle secretion, including: (i) four arginine residues (aa 17-22) comprising the basic region; (ii) a phosphofurin acidic cluster sequence (PACS; Glu61-64); and (iii) a secretion modification region (SMR) spanning amino acid residues 65-70 (VGFPV). Additional amino acids associated with Nef secretion include $P_{25,\ 29}GVG_{31}$, and T44. The portion of HIV-1 Nef containing the amino acids 1-70 was found to be sufficient to drive Nef-induced vesicle secretion in all cell types tested.

SMS allows other proteins to be released into the supernatant. The green fluorescent protein (GFP) gene was cloned downstream of the HIV-1 Nef sequences such that a Nef-GFP fusion protein would be expressed. Nef sequences were able to drive secretion of GFP into the extracellular supernatant in vesicles. The conditioned supernatant was assayed for GFP expression by a fluorescent plate reader assay. The GFP clone alone is not secreted into the extracellular supernatant. HIV-1 Nef Δ71-206-GFP, containing only the N-terminal 70 amino acids of HIV-1 Nef protein, secretes GFP into the conditioned supernatant in vesicles as well as the full wtNef-GFP construct. Red fluorescent protein (RFP) fused to these same Nef sequences can also be secreted into the conditioned supernatant in vesicular format. Thus, Nef N-terminal sequences are useful for redirecting exogenous proteins into vesicles, which are released from the cell they are expressed in.

Materials and Methods

Cells and reagents. *Escherichia coli* STBL-2 cells (Invitrogen, Palo Alto, CA) were maintained in LB broth or LB agar (Becton, Dickinson and Company, Sparks, MD) plates at 30° C. and plasmid-containing transformants were selected on LB agar plates containing ampicillin (100 μg/ml). Jurkat CD4+ T cell lines derived from human T cell leukemia and human cutaneous T cell lymphoma cells, respectively, were obtained from the NIH AIDS Research and Reference Reagent Program (ARRRP). THP-1 and U-937 monocytic leukemia cell lines were obtained from the American Type Culture Collection (Manassas, VA). Cells were maintained in RPMI 1640 medium (Invitrogen) supplemented with streptomycin (100 U/ml), penicillin (100 U/ml), $_L$-glutamine (2.0 mM), and HEPES-buffered saline solution (10 μM). HEK293 cells derived from a human primary embryonic kidney transformed by adenovirus type 5 were obtained from the NIH ARRRP. The cells were maintained in 5% fetal bovine serum HEK293 medium (Invitrogen) supplemented with streptomycin (100 U/ml) and penicillin (100 U/ml). FRhK-4 (rhesus monkey epithelial cells) cells were maintained in DMEM with penicillin (100 U/ml)/streptomycin (100 U/ml), 4.0 mM $_L$-glutamine, 4500 mg/liter glucose, 1.0 mM sodium pyruvate, 1500 mg/liter sodium bicarbonate, and 10% fetal bovine serum. The cells were incubated at 37° C. for 2-4 days and were harvested when they reached 80-90% confluence.

The following antibodies were used: (1) rabbit polyclonal anti-GFP antibody (Abcam, Inc., Cambridge, MA), (2) rabbit polyclonal anti-Nef antibody (NIH ARRRP) and murine monoclonal anti-Nef HIV-1 antibody (ImmunoDiagnostic, Inc., Woburn, MA), (3) monoclonal anti-CD45 antibody (Abcam Inc., Cambridge, MA); (4) monoclonal anti-AChE antibody (Chemicon, Temecula, CA), (5) rabbit monoclonal anti-GFP antibody (Abcam Inc., Cambridge, MA), (6) goat anti-Alix polyclonal antibody (Santa Cruz, Inc., Santa Cruz, CA), (7) monoclonal antitubulin antibody (Sigma, St. Louis, MO), (8) goat antirabbit IgG (H+L) labeled with horseradish peroxidase (HRP; Pierce, Rockford, IL), (9) camptothecin (Sigma, St. Louis, MO), and (10) donkey antigoat IgG-HRP (Santa Cruz, Inc., Santa Cruz, CA).

Construction of the Nef mutants. The HIV-1 NL4-3 nef construct in expression vector pQBI-Nef-GFP (Quantum Biotechnologies, Montreal, Canada) was used as a template for amplifying various Nef amplicons as well as for the subcloning of the Nef mutants to create Nef-GFP fusion constructs (FIG. 1). Nef-GFP was expressed under the control of the CMV promoter in pQBI in the various cell types tested (HEK-293, FRhK-4, Jurkat T cells and monocytes, THP-1/U937).

Deletion mutants of the C-terminus of HIV-1 Nef (FIG. 4A) Δ31-206, Δ51-206, Δ66-206, Δ71-206, Δ91-206, Δ151-206, and Δ201-206 were constructed by polymerase chain reaction (PCR) amplification using primers Nef-R-5798-NheI-F, Nef-R-5735-NheI-F, Nef-R-5690-NheI-F, Nef-R-5675-NheI-F, Nef-R-5615-NheI-F, Nef-R-5435-NheI-F, and Nef-R-5285-NheI-F, respectively, in combination with Nef-R-541-PvuI-R1 for PCR (see Table 1). The resulting amplicons had NheI and PvuI restriction enzyme sites on each flank. These amplicons were subsequently cloned into the NheI/PvuI sites in the pQBI vector. N-terminal deletion mutants of HIV-1 Nef Δ1-12 and Nef Δ1-40 were constructed with primers Nef13-F-SacII and Nef41-F-SacII, respectively, in combination with GFP-R-EcoRI for PCR amplification (see Table 1). The resulting amplicons had SacII and EcoRI restriction enzyme sites on each flank for subcloning into the pQBI-GFP SacII/EcoRI sites. To obtain the Δ1-12/Δ1-40 deletion mutants in the context of a full-length Nef gene, the pQBI-Nef-GFP was used as a DNA template whereas to obtain the Δ1-12/Δ1-40 in the context of the first HIV Nef 70 aa, pQBI-Nef 1-70-GFP was used as a DNA template.

For the construction of HIV-1 substitution mutants (FIG. 4B) Nef-EEEE/4A-GFP, NefR/4A-GFP, NefK/P-GFP, NefS/A-GFP, and NefVGFPV-GFP, primers PACS-F/PACS-R, RXRXRR-F/RXRXRR-R, XKX-F/XKX-R, XSSX-F/XSSX-R, and VGFPV-F/VGFPV-R (Table 1), respectively, were used for site-directed mutagenesis in combination with the QuikChange Site-Directed Mutagenesis Kit (Stratagene, La Jolla, CA). A GFP expression plasmid (pQBI-GFP) was constructed by amplifying GFP using GFP-1-F-SacII/GFP-R-EcoRI primers (Table 1). The amplicon had SacII and EcoRI restriction enzyme sites on each flank for subcloning into SacII/EcoRI sites of the pQBI vector to yield pQBI-GFP.

All of the HIV Nef-GFP constructs used in this study were confirmed by sequencing of both DNA strands using CMV-846-F and GFP-1855-R primers, respectively (Table 1).

TABLE 1

PCR and Site-Directed Mutagenesis Primers Used in Example 1

| Primer | Sequence |
|---|---|
| CMV-846-F | CGTGTACGGTGGGAGGTCTATATAAGC (SEQ ID NO: 8) |
| GFP-1855-R | CATAACCTTCGGGCATGGCACTC (SEQ ID NO: 9) |
| Nef-R-5798-NheI-F | CATTGCTAGCCCCATCTGCTGCTGGCTCAGC (SEQ ID NO: 10) |
| Nef-R-5735-NheI-F | CATTGCTAGCAGCTGCTGTATTGCTACTTGTGATTGC (SEQ ID NO: 11) |
| Nef-R-5690-NheI-F | CATTGCTAGCCTCTTCCTCCTCTTGTGCTTCTAGC (SEQ ID NO: 12) |
| Nef-R-5675-NheI-F | CATTGCTAGCGACTGGAAAACCCACCTCTTCCTC (SEQ ID NO: 13) |
| Nef-R-5615-NheI-F | CATTGCTAGCAAAGTGGCTAAGATCTACAGCTGCCTT (SEQ ID NO: 14) |
| Nef-R-5435-NheI-F | CATTGCTAGCTGGCTCAACTGGTACTAGCTTGTAGCA (SEQ ID NO: 15) |
| Nef-R-5285-NheI-F | CATTGCTAGCCGGATGCAGCTCTCGGGCCA (SEQ ID NO: 16) |
| Nef-R-541-PvuI-R1 | GGTCCTCCGATCGTTGTCAGAAGT (SEQ ID NO: 17) |
| Nef13-F-SacII | CAGTCCGCGGATG TGGCCTGCTGTAAGGGAAAGAATG (SEQ ID NO: 18) |
| Nef41-F-SacII | CAGTCCGCGGATG GGAGCAATCACAAGTAGCAATACAGCA (SEQ ID NO: 19) |
| PACS-F | CTAGAAGCACAAGCGGCGGCAGCGGTGGGTTTTCCA (SEQ ID NO: 20) |
| PACS-R | TGGAAAACCCACCGCTGCCGCCGCTTGTGCTTCTAG (SEQ ID NO: 21) |
| RXRXRR-F | ATGTGGCCTGCTGTAGCGGAAGCAATGGCAGCAGCTGAGCCAGCA (SEQ ID NO: 22) |
| RXRXRR-R | TGCTGGCTCAGCTGCTGCCATTGCTTCCGCTACAGCAGGCCACAT (SEQ ID NO: 23) |
| XKX-F | GCAGTATCTCGAGACCTAGAACCGCATGGAGCAATCACAAGTAGC (SEQ ID NO: 24) |
| XKX-R | GCTACTTGTGATTGCTCCATGCGGTTCTAGGTCTCGAGATACTGC (SEQ ID NO: 25) |
| XSSX-F | CATGGAGCAATCACAGCCGCGAATACAGCAGCTAAC (SEQ ID NO: 26) |
| XSSX-R | GTTAGCTGCTGTATTCGCGGCTGTGATTGCTCCATG (SEQ ID NO: 27) |
| XEEEX-F | TGGCTAGAAGCACAAGACGACGACGACGTGGGTTTTCCAGTC (SEQ ID NO: 28) |
| XEEEE-R | GACTGGAAAACCCACGTCGTCGTCGTCTTGTGCTTCTAGCCA (SEQ ID NO: 29) |
| VGFPV-F | CAAGAGGAGGAAGAGGCGGCTGCTGCAGCCGCTAGCAAAGGAGAA (SEQ ID NO: 30) |
| VGFPV-R | TTCTCCTTTGCTAGCGGCTGCAGCAGCCGCCTCTTCCTCCTCTTG (SEQ ID NO: 31) |
| GFP-1-F-SacII | CAGTCCGCGGATGGCTAGCAAAGGAGAAGAACTCTTCACT (SEQ ID NO: 32) |
| GFP-R-EcoRI | TGCAGAATTCCAGCACACTGG (SEQ ID NO: 33) |
| GFP-1-F-SacII | CAGTCCGCGGATG GCTAGCAAAGGAGAAGAACTCTTCACT (SEQ ID NO: 34) |
| GFP-R-EcoRI | TGCAGAATTCCAGCACACTGG (SEQ ID NO: 35) |
| Cherry-F-NheI | CGCG GCTAGC TCATCT GTGAGCAAGGGCGAGGAGGAT (SEQ ID NO: 36) |
| Cherry-R-BamHI | CGCG GGATCC TCA CTTGTACAGCTCGTCCATGCC (SEQ ID NO: 37) |
| Cherry-F-HindIII | CGCG AAGCTT ATG GTGAGCAAGGGCGAGGAGGAT (SEQ ID NO: 38) |

[a]All primers are from 5' to 3' orientation.

Cell Transfection. HEK293cells were grown in serum-free medium (GIBCO 293 Freestyle, Invitrogen) at 37° C. to a confluence of 75-80%. Cells were trypsinized, washed, and counted before transfection with wtNef-GFP and Nef mutants using electroporation (Bio-Rad Model 1652108). Jurkat, FRhK-4, THP-1, and U937 monocytes were grown in serum-free RPMI 1640 medium and then diluted to a final concentration of $1\times10^6$ cells/100 μl of medium and mixed with 1 μg of plasmid DNA. The cells were transferred to electroporation cuvettes (2 mm, Bio-Rad), pulsed at 140V (Jurkat), 130V (FRhK-4), and 140V (THP-1 and U937 monocytes) using a Bio-Rad Model Gene Pulser Xcell system, following the manual to select conditions. The cell/DNA solution was then centrifuged at 600×g for 5 min, the floating dead cells were removed, and the pellet was resuspended in 1 ml of fresh media containing 5% fetal bovine serum (FBS). The cells were put in culture plates and incubated for 48 h at 37° C. Cells were collected by centrifuging at 600×g for 5 min. The cells were mounted on a slide and the transfection efficiency was calculated by counting the green fluorescent cells using a fluorescent microscope.

Propidium iodide (PI) assay. HEK293 cells were transfected with pQBI/HIV-1 Nef mutant plasmid DNA for 48 h as described above. The cells were washed in PBS after which freshly prepared PI solution (1.25 μg/ml) was added. The cells were incubated at room temperature for 2 min and examined immediately under a microscope, with dead cells staining red.

TUNEL assay. The HEK293 cells were transfected with pQBI/HIV-1 wtNef-GFP or wtNef-RFP plasmid DNA for 48 h as described above. The cell cultures were assayed for apoptosis by TUNEL assay, by epifluorescence detection, on a computer-controlled fluorescence microscope system (Carl Zeiss, Thornwood, NY). Cells transfected with wtNef-RFP were visualized as red, whereas the TUNEL-labeled apoptotic cells were green.

Exosome isolation and purification from the transfected cells. Cells transfected with HIV-1 wtNef-GFP ($10^6$ cells/ml, as described above) were harvested at 48 h posttransfection. The cells were removed from the culture media by centrifugation at 600×g for 5 min. The cell-free supernatant was subjected to a second spin at 10,000×g for 30 min to pellet the cell debris. Exosomes were collected by sequential centrifugations of this cleared supernatant at 50,000×g for 45 min, 100,000×g for 1 h, and 400,000×g for 2 h at 4° C. As a negative control, culture media from a similar volume of untransfected cells were also subjected to sequential centrifugations. It was further determined that exosome-like vesicles could be isolated from untransfected Jurkat cells by starting with conditioned media from a larger number ($2.5\times10^7$ cells) of cells using the same procedure.

Exosome flotation on continuous sucrose gradients. Jurkat cell cultures were transfected and distributed in 35-mm dishes (1 ml/dish) as described. For the preparation of exosomes on flotation gradients, 28 ml of untransfected Jurkat cell cultures and 14 ml of HIV-1 wtNef-GFP-transfected Jurkat cell cultures were centrifuged for 5 min at 600×g to remove the cells. The cell pellets (see FIG. 2, lane 1) were set aside for processing (SDS PAGE and Western blot, described below). The cell-free supernatants were then centrifuged for 10 min at 1200×g and an aliquot (4 ml untransfected and 1 ml wtNef-GFP-transfected) of this 1200×g clarified supernatant (see FIG. 2, lane 2) was also processed for Western blotting. The remaining clarified supernatants (24 ml untransfected and 12 ml wtNef-GFP-transfected) were subjected to sequential centrifugation for 30 min at 10,000×g, 45 min at 50,000×g, 60 min at 200,000×g, and 60 min at 400,000×g, using a Type 42.1 ultracentrifuge rotor (Beckman Instruments, Inc., Fullerton, CA). The 50,000×g pellets were saved for Western blotting (see FIG. 2, lane, 3). The 200,000×g and 400,000×g pellets were resuspended in 1 ml of 2.5 M sucrose, 20 mM HEPES/NaOH, pH 7.2. An aliquot (250 μl) of each sucrose suspension was centrifuged at 400,000×g for 60 min. These samples (see FIG. 2, lane 4) were set aside for Western analysis. A 10-ml linear sucrose gradient (2.0-0.25 M sucrose, 20 mM HEPES/NaOH, pH 7.2) was layered on top of the remaining 750 μl of sucrose suspension in a Beckman Ultra-Clear 14×95-mm tube and centrifuged at 100,000×g for 16 h using a Type 40-Ti rotor (Beckman Instruments, Inc.). Gradient fractions (12 fractions of 750 μl) were collected, subsequently diluted 1:3 with phosphate-buffered saline (PBS), and centrifuged for 60 min at 400,000×g using a TLA 100.4 rotor (Beckman Instruments, Inc.). The resultant pellets (gradient fractions; (see FIG. 2, lanes 5-12) were set aside for Western blot analysis.

Processing of fractions for SDS-PAGE. Aliquots of the 1200×g clarified supernatants from untransfected and wtNef-GFP-transfected cultures and the fractions from the other steps were centrifuged at 400,000×g. The pellets were collected and lysed in 2×SDS-PAGE sample buffer and heated at 95-100° C. for 5 min. The 400,000×g spent supernatants after differential centrifugation were processed by trichloracetic acid (TCA) and acetone precipitation. TCA was added to each supernatant to a final concentration of 15% and the precipitates were allowed to form at 4° C. overnight. Precipitated proteins were collected by centrifugation at 16,000×g for 30 min and the pellets were washed twice with ice-cold acetone and finally resuspended in 2×SDS sample buffer for analysis.

Fluorescent plate reader assay. One hundred microliters of cell-free conditioned media was transferred to each well of a 96-well black microtiter plate (Corning Incorporated, NY). These were assayed for fluorescence on a Tecan GENEios fluorimeter (Tecan Group, Switzerland) with excitation wavelength 485 nm and emission wavelength 515 nm. Conditioned media from pQBI-GFP-transfected and untransfected cells were used as positive and negative control, respectively.

Immunoblot analysis. Cells and vesicle proteins were analyzed by Western blot analysis. The cell or vesicles protein samples were separated by SDS-PAGE on a 4-20% Tris-HCl Criterion precast gel (Bio-Rad Laboratories, Hercules, CA) and electrophoretically transferred to the nitrocellulose membrane. The membrane was washed in Tris-buffered saline (TBS) for 5 min, blocked with 5% nonfat milk in TTBS (TBS with 0.1% Tween 20) for 1 h by shaking at room temperature, processed for immunoblotting using a specific first primary antibody with shaking at 4° C. overnight, followed by a secondary HRP-conjugated IgG (H+L) antibody. Protein bands were detected by Western Blotting Luminol Reagent (Santa Cruz Biotechnology, Inc., Santa Cruz, CA) followed by an exposure to photographic film (BioMax film; Fisher Scientific, Pittsburgh, PA). In some experiments, the membrane was stripped using a stripping reagent (Pierce, Rockford, IL) and used to hybridize with a different primary and secondary antibody. The X-ray films were scanned into Adobe Photoshop 5.0.2 and arranged for publication in Adobe Illustrator 10 (Adobe Systems, San Jose, CA).

Nef protein sequence alignment. The consensus Nef amino acid sequence for each HIV-1 clade (A through O) was determined by alignment of individual Nef variant sequences downloaded from the HIV Sequence Database (Los Alamos National Laboratory) using the algorithms in GENEious Pro 4.0.2 (Biomatters Ltd., Auckland, NZ). Specifically, alignments were generated using a Blosum62 Cost Matrix, with a gap opening penalty=12 and gap extension penalty=3. The 13 HIV-1 clade consensus sequences thus determined were then submitted for alignment in GENEious Pro, using the same parameters.

Data analysis. The numerical and graphic analyses of all data obtained were obtained through analysis using at least three repetitions of each experiment. Data were calculated and graphs were generated using SigmaPlot 10 (Systat, San Jose, CA). One-sided Student's t-test analysis was used to compare data conditions.

Exosome secretion. As shown in FIG. 1, when Nef-GFP is transfected in Jurkat cells, AChE and CD45 (exosomal marker proteins) are released also. This suggests that more of these two proteins were secreted from Nef-GFP-transfected cells (FIG. 1B, lower panel set; FIG. 1C) than from untransfected cells (FIG. 1B, top panel set; FIG. 1C). Nef-GFP-transfected cells also display an increase in intracellular AChE and CD45 concomitant with AChE release (FIG. 1A, UT vs. Nef, AChE; FIG. 1C) or CD45 release (FIG. 1A, UT vs. Nef, CD45; FIG. 1C) while no change in intracellular tubulin is observed (FIG. 1A, UT vs. Nef, tubulin). This clearly establishes a Nef protein-induced increase in intracellular AChE and CD45 concomitant with release of Nef, AChE, and CD45 in high-molecular-weight format. This is consistent with intracellularly expressed Nef-inducing secretion of vesicles containing Nef, AChE, and CD45.

Nef protein is found in vesicular form and not in soluble form. If Nef is associated with vesicles, some fraction of the secreted material should be membrane associated. This can be demonstrated by subjecting the pelleted material from the cell supernatants to membrane flotation. Thus, Jurkat cell cultures were transfected with pQBI-Nef-GFP expressing full-length HIV-1 NL4-3 Nef, and the conditioned media from these and from untransfected cells were collected, lysed, assayed for total protein, and stored for Western analysis. Conditioned cell media were spun at 1200×g for 10 min, the supernatant was collected, and an aliquot of this was set aside for Western analysis. The bulk of the material was subjected to differential centrifugation at 10,000×g, 50,000×g, 200,000×g, and 400,000×g and the pellets from each spin were collected. The 50,000×g pellet was set aside to be assayed, aliquots of the 200,000×g and 400,000×g pellets were set aside for assay, and the bulk of these two pellets was loaded onto sucrose gradients and subjected to flotation centrifugation. Fractions from each gradient were collected and were assayed. Finally, the spent supernatant from the 400,000×g differential centrifugation step was TCA precipitated and the pellet was resuspended in a small volume to be assayed. Each of these collected samples was assayed by SDS-PAGE and Western analysis probing for Nef, GFP, and Alix, an exosomal marker. Representative Western blot images for untransfected cultures and NefGFP-expressing cultures are shown in FIG. 2A with collated densitometric measurements of multiple gradients shown in FIG. 2B.

As shown in FIG. 2B, all of the Nef protein in the conditioned cell media was pelleted in the differential centrifuge steps and was found in the floated fractions of the flotation gradients. In contrast, no (soluble) Nef protein or GFP was detected in the 400,000×g spent supernatant fraction (data not shown). Second, in the flotation gradients of pelleted vesicles, the peak band densities for Nef, GFP, and Alix were detected in gradient fractions 6-8 (FIG. 2B, lanes 7-9). The vesicle preparations floated at a sucrose density of 1.11-1.17, which is similar to flotation data reported for exosomes from B-lymphocytes (Raposo et al., *J. Exp. Med.,* 183(3):1161-1172, 1996). Third, the amount of Alix (as measured by band densities) in all four fractions assayed was larger in the Nef-GFP-expressing cultures than in the untransfected cultures (FIG. 2B; all p values were less than 0.01). Furthermore, the difference in amount of Alix in Nef-GFP expressing vs. untransfected cell lysates and supernatants was smaller than that observed for untransfected cell lysates vs. supernatants (FIG. 2B). Finally, Nef, GFP, and Alix densitometric measurements in the differential centrifugations and the sucrose flotation gradient were found to be approximately equivalent. All this suggests that Nef increases intracellular expression of at least some specific proteins, and is released from transfected cells in vesicular form and in vesicles containing the exosomal marker Alix.

The genetics of exosome secretion. The N-terminal 70 amino acids of Nef are sufficient to induce secretion. As shown above, Nef-GFP transfected into cells appears to induce release (secretion) of itself in high-molecular-weight form along with AChE and CD45. This suggests that sequences or motif(s) on Nef protein actively induce and regulate this release/secretion function. Truncation mutants deleting various lengths of the C-terminal region NefΔ31-206GFP, NefΔ51-206GFP, NefΔ71-206GFP, NefΔ91-206GFP, NefΔ151-206GFP, and NefΔ201-206GFP (FIG. 4A) —were developed to examine their ability to induce secretion of Nef-GFP into the conditioned media using transient transfection of HEK293 cells (FIG. 6A). The clone pQBI-Nef-GFP (wt in FIG. 6A), containing the full-length HIV-I NL4-3 Nef, was used as a positive control, while pQBI-GFP, containing only the GFP sequence, was used as a negative control in some experiments. Media collected from the cells transfected with pQBI-NefΔ71-206GFP (1-70 in FIG. 6A), pQBI-NefΔ91-206GFP (1-90 in FIG. 6A), pQBI-NefΔ151-206GFP (1-150 in FIG. 6A), and pQBI-NefΔ201-206GFP (1-200 in FIG. 6A) displayed fluorescence comparable to the cells transfected with full-length nef-containing plasmid. Alternatively, conditioned media from cells transfected with pQBI-NefΔ31-206GFP (1-30 in FIG. 6A) and pQBI-NefΔ51-206GFP (1-50 in FIG. 6A) displayed only background levels of fluorescence comparable to the negative control. These results showed that the N-terminal 70 aa of HIV-1 Nef were sufficient to induce secretion of the Nef-GFP protein into the conditioned media.

Figure 4A:
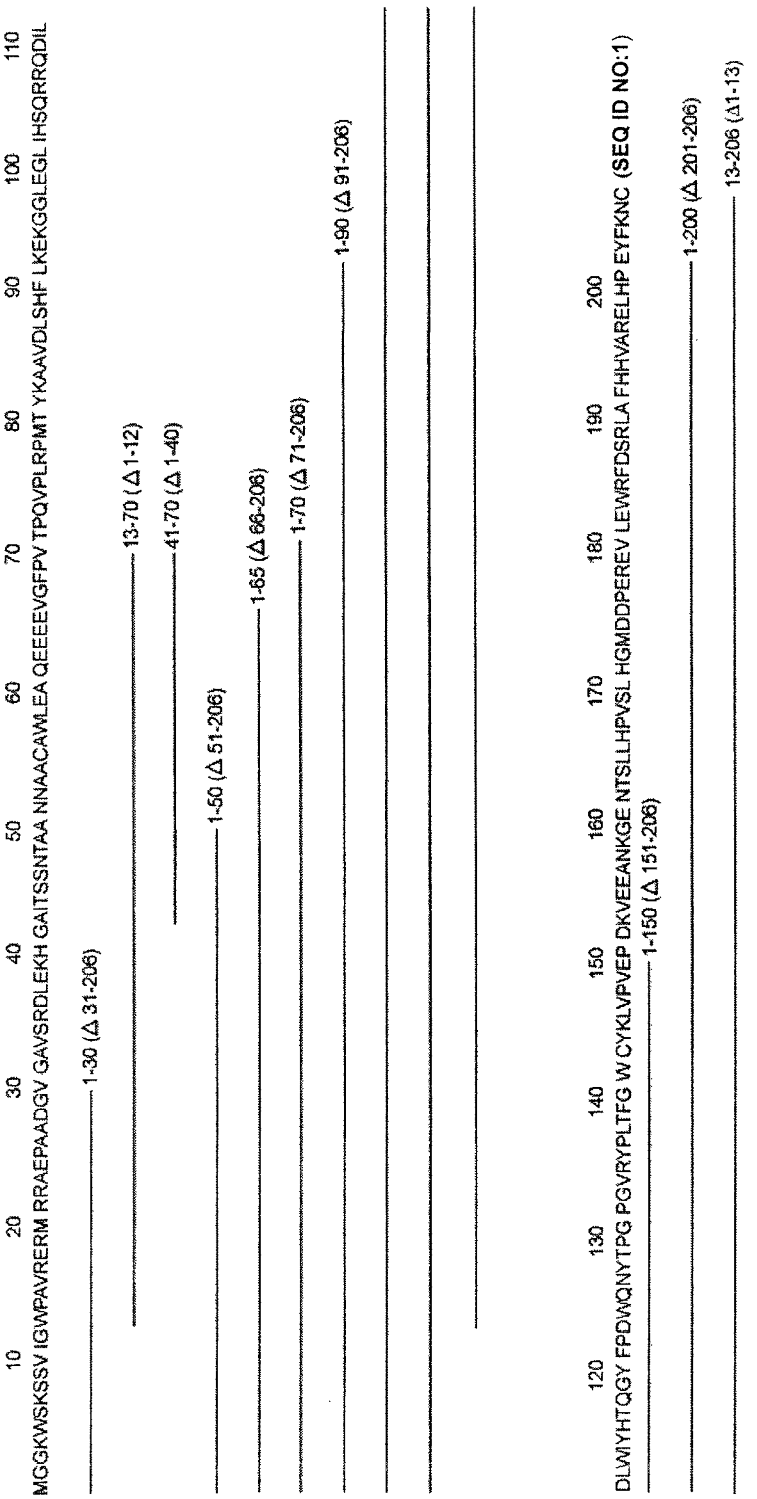
FIGS. 4A-B show a schematic representation of HIV NL4-3 Nef mutants generated for testing.
Figure 4B:
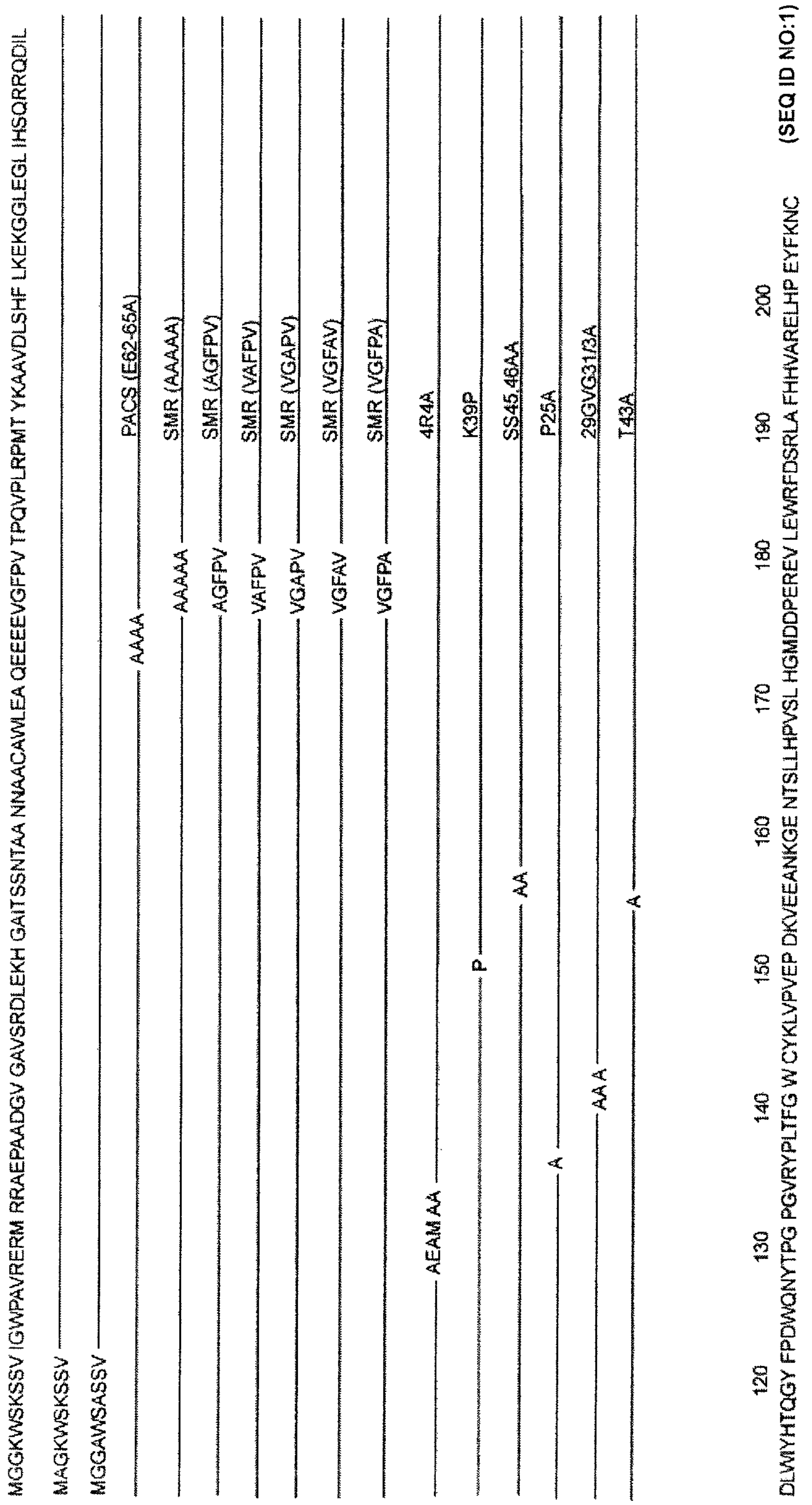

The PACS motif ($^{62-65}$E) was required for Nef-induced vesicle secretion. Because the first 70 amino acids of Nef were sufficient for the secretion of Nef-GFP but the first 50 amino acids were not, it was anticipated that a secretion regulatory motif was within amino acids 50-70. There were two known motifs within this 20-amino acid region: (1) amino acids 51-61 are the apoptotic motif (James et al., *J. Virol.,* 78(6):3099-3109, 2004) and (2) amino acids 62-65 are the phosphofurin acidic cluster sequence (PACS) motif (Piguet et al., *Nat. Cell Biol.,* 2(3):163-167, 2000). The PACS replacement mutant clone pQBI-Nef$^{62}$EEEE$^{65}$/4AGFP (PACS in FIG. 6B) was constructed by replacing the four glutamic acid residues with four alanine residues as described in Materials and Methods (FIG. 4B). As shown in FIG. 6B, conditioned media collected from cells transfected with pQBI-Nef$^{62}$EEEE$^{65}$/4AGFP had only background fluorescence whereas pQBI-Nef6,71-206GFP (1-70 in FIG. 6B) had fluorescence comparable to that of pQBI-NefGFP (wt in FIG. 6B). This result suggested that the PACS region of HIV-1 Nef is a secretion regulatory motif.

The helix-1 domain but not the myristoylation domain is required for Nef secretion. Within the N-terminal 70 amino acids, five distinct motifs have been identified as being involved in membrane interactions (FIG. 5A). These include the myristoylation region (amino acid 2), basic amino acid region 1 (BAA-1; Lys4 and Lys7), basic amino acid region 2 (BAA-2; Arg17, 19, 21, 22), which overlaps with helix-1 (Trp13-Arg21), the helix-2 (Ser34-Gly41; Geyer et al., *J. Mol. Biol.,* 289(1):123-138, 1999) and the plasma membrane targeting domain (PMTD, Gly41-Ala60). Similar domains are also found in SIV-Nef (FIG. 5B). It was possible that these or other as yet unidentified domains were also required for Nef-induced secretion. Several truncation mutants with N-terminal amino acids deleted (pQBI-Nef Δ1-12GFP and pQBI-Nef Δ1-40GFP) were constructed by deleting 1-12 aa (myristoylation region and BAA-1 were deleted) and 1-40 aa (BAA-2/helix-1 and helix-2 were deleted), respectively. No fluorescence was observed in the conditioned media collected from cultures transfected with pQBI-Nef Δ1-40GFP (41-70 in FIG. 6A), but conditioned media from pQBI-Nef Δ1-12GFP (13-206 in FIG. 6A), pQBID1-12/D71-206GFP (13-70 in FIG. 6A), and pQBI-NefΔ71-206GFP (1-70 in FIG. 6A) exhibited fluorescence intensity comparable to that of pQBI-NefGFP (wt in FIG. 6A). Cultures transfected with the mutant pQBI-NefG2A (G2A in FIG. 6B) and pQBI-NefK4K7/2A (NefK4K7 in FIG. 6B) also displayed fluorescence levels comparable to the wild-type construct, confirming the data obtained with deletion constructs. This indicated that the myristoylation domain and basic region 1 were not involved in Nef-induced secretion, whereas either the helix-1 or -2 regions, or another, as yet, unidentified domain between 13 and 41 aa was required for the secretion.

The basic amino acid motif in helix-1 is required for secretion. To determine what domain(s) between 13 and 41 aa was required for the secretion, several mutant clones were constructed (FIG. 4B). These were pQBI-Nef$^{17,19,21,22}$R/4AGFP, in which the four basic arginines of BAA-2/helix-1 were replaced with four alanines; pQBI-NefK/PGFP, in which a proline was inserted in place of $^{39}$K as a helix breaker in helix-2; and pQBI-Nef$^{45,46}$S/AGFP, in which the PMTD was mutated replacing the two serines at positions 45 and 46 with two alanines. The mutations in pQBI-Nef$^{39}$K/PGFP (FIG. 6B, K39P) and pQBI-Nef$^{45,46}$S/AGFP (FIG. 6B, SS4546AA) had no effect on secretion of fluorescence in the conditioned media from transfected cultures comparable to that of the pQBI-NefΔ71-206GFP (FIG. 6B, 1-70) or pQBI-NefGFP (FIG. 6B, wt). Cultures transfected with pQBI-Nef17,19,21,22RAAGFp (FIG. 6B, 4R4A) had significantly decreased fluorescence in the conditioned media suggesting that basic region 2 in helix-1 is important for Nef secretion.

Other previously unexplored sequences on Nef are required for secretion. To determine the minimum N-terminal sequence required for secretion we constructed a C-terminal truncation removing all amino acids after the PACS motif (pQBI-NefΔ66-206GFP; FIG. 4A). A significant decrease in the fluorescence in the conditioned media from cells transfected with this construct was observed (FIG. 6A, 1-65). This suggested that a third secretion regulatory motif lay within the amino acids 66-70 (VGFPV; see FIG. 5A). Using an alanine replacement mutant clone, pQBI-Nef$^{66}$VGFPV$^{70}$GFP, with amino acids $^{66}$VGFPV$^{70}$ replaced with five alanines, significantly decreased fluorescence was observed in conditioned media collected from these cultures (FIG. 6B, VGFPV/5A). Thus, this region, a domain not previously described in the literature that we named the secretion modification region (SMR), is a third region important for Nef secretion.

A phylogenetic analysis of HIV-1 Nef amino acids 1-70 intra-B-clade and across all HIV-1 clades found that the secretion domains are highly conserved within the SMR region. with the newly identified. The SMR was 100% conserved across all HIV-1 clades. This evidence indicates the relevance of these domains, particularly in a virus that displays high sequence variability. Further, domain conservation was also found to apply when the N-terminal sequences of HIV-1 and SIV were compared (data not shown). Although most of the Nef secretion regulatory sequences were found in the Nterminal 102 amino acids of SIV Nef, the three functional motifs in association with Nef secretion in high-molecular weight form are very similar to HIV and comprise two BAA regions, a PACS domain and an SMR-like region located immediately downstream of the PACS.

To characterize the SMR more fully, an individual alanine replacement analysis was performed. Five clones were developed containing the full-length nef gene with nucleotides coding for one of the five amino acids of the SMR replaced with nucleotides for alanine (see FIG. 4B; lanes 5-9). Alanine replacement mutants V66A, G67A, and V70A each displayed only background levels (FIG. 6C, AGFPV, VAFPV, VGFPA; 1.8%, 2%, 1.9%, respectively), similar to the ones measured by the pQBI-GFP-negative control (FIG. 6C, pQBI-GFP; ~1.7%), of extracellular fluorescence in the conditioned media collected from the transfected cultures. Alanine replacement mutant P69A displayed a small but reproducible amount of extracellular fluorescence (FIG. 6C, VGFAV; ~6%) compared to the positive control. Alanine replacement mutant F68A displayed a reduced but significant amount of extracellular fluorescence (FIG. 6C, VGAPV; ~30%) in the conditioned media as compared to the positive control. Thus, three of the five amino acids are critical for secretion, with single mutations in any one of those three leading to complete elimination of the ability of Nef to induce secretion of itself in vesicles.

The amino acids between R22, the C-terminal amino acid in the BAA-2 motif in helix-1 and E62, the N-terminal amino acid in the PACS domain, were also screened using alanine replacement identifying several amino acids that influence secretion. These clones were developed in the full-length nef background. The pQBI-NefP25A-GFP clone (FIG. 4B) displayed background amounts of extracellular fluorescence (FIG. 6B, P25A; ~4%) in the conditioned media as compared to the positive control. pQBI-Nef$^{29}$GVG$^{31}$3A (FIG. 4B) and pQBI-NefT44A-GFP clone (FIG. 4B) also displayed background amounts of extracellular fluorescence (FIG. 6B, 29GVG31/3A, 4%; T44A, 4% respectively).

These domains are relevant in other cell lineages. The initial secretion analysis described above was performed in HEK293 cells. These cells are easily transfectable and do not normally secret vesicles. Thus, they are optimal for viewing secretion and identifying changes in the secretion ability although not a normal target for viral infection. More appropriate would be Nef secretion analysis of these constructs in either lymphocytic or monocytic cell lines as these lineages are targets of HIV infection. Specific Nef mutants described above were analyzed in a lymphocytic cell line (Jurkat cells) and in two monocytic lines (THP-1 and U937 cells; FIG. 6). The pQBI-Nef$^{17,19,21,22}$R/4AGFP mutant clone (BAA-2 region knockdown), the pQBI-Nef$^{62}$EEEE$^{65}$/4AGFP mutant clone (PACS region knockdown), and the pQBI-Nef$V^{65}$AGFP mutant clone (SMR region substitution mutation knockdown) all displayed extracellular fluorescence levels in lymphocytic and monocytic cells similar to those observed in HEK293 cells. There was some variation in the extracellular fluorescence levels of the truncation mutant's transfected in lymphocytic (FIG. 6D, 1-70, 13-70, 13-206) and monocytic cell lines (FIG. 6E or 6F, 1-70, 13-70, 13-206) relative to each other or to HEK293 cells (FIG. 6A, 1-70, 13-70, 13-206). However, the variations observed were not significant and the trend for each of these truncation mutants was for them to display wild-type or close to wild-type levels of fluorescence.

Phylogenetic analysis across HIV clades. The genetic analysis of Nef secretion was performed using HIV-1 NL4-3 Nef. A logical next step was to determine the conservation of the identified secretion domains across HIV B Glade viruses and across the other HIV-1 clades uncovering the relative importance of these domains. An analysis of that region of Nef involved in secretion (amino acids 1-70) demonstrates significant sequence conservation within the secretion domains across all HIV-1 clades (FIG. 7). Interestingly, the SMR domain, which was always found contiguous to and C-terminal of the PACS domain, displayed 100% sequence conservation across all the HIV clades suggesting the importance of these sequences.

HIV Nef expressed in cells is not toxic/apoptotic to transfected cells. One alternative explanation of the effects being observed is that endogenous Nef protein causes toxicity to the cells in which it is expressed, leading to those cells releasing Nef protein in apoptotic microvesicles or microparticles. Prior studies of cells releasing putative exosomes have shown that cells in the early stages of apoptosis release membrane vesicles that are very similar to vesicles released by healthy cells (e.g., exosomes; Thery et al., *J. Immunol.,* 166(12):7309-7318, 2001; Aupeix et al., *J. Clin. Invest.,* 99(7):1546-1554, 1997). However, the protein composition of the apoptotic vesicles was different from that of the exosomal vesicles. For example, the apoptotic vesicles contained large amounts of histones as opposed to little or no histone protein found in the exosomal vesicles.

It was previously shown that soluble recombinant Nef (rNef) protein and the conditioned supernatant from Nef-transfected cells are apoptotic to naive cells expressing CXCR4 (Huang et al., *J. Virol.,* 78(20):11084-11096, 2004). Thus, it is possible that these Nef-containing vesicles represent apoptotic vesicles. To evaluate this possibility, cells were transfected with the various Nef-GFP constructs for cell death and apoptosis (FIG. 8) and the supernatant/vesicles released from the Nef-transfected cells were examined for histone content in the vesicles, a marker of apoptotic vesicles (FIG. 9).

Figure 8A:
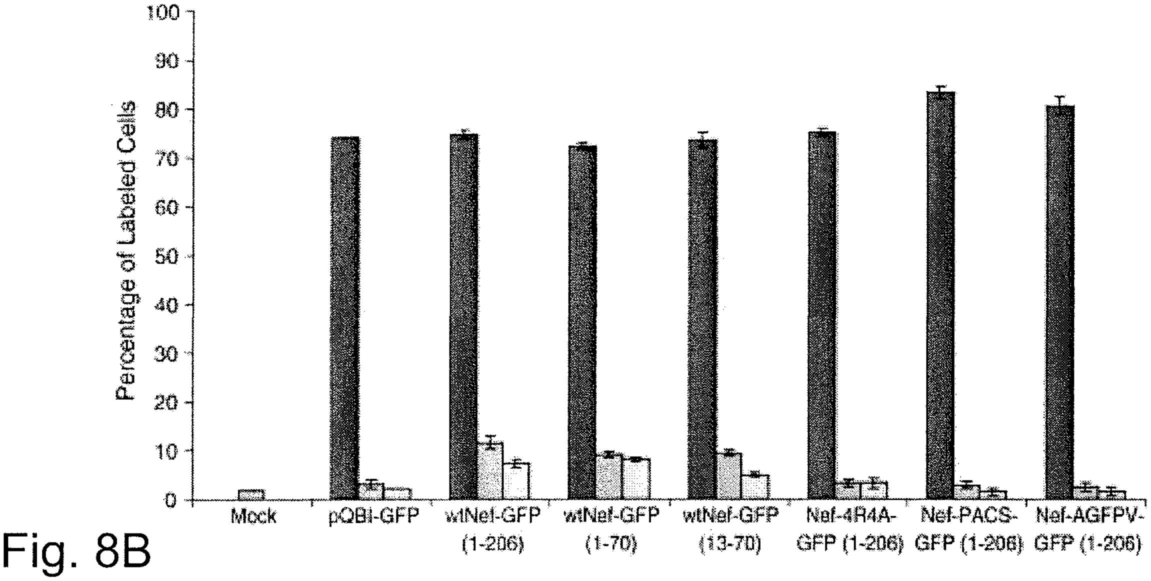
FIGS. 8A-B shows that HIV Nef expression in cells is not toxic or apoptotic to transfected cells. HIV-1 Nef-GFP mutants were transfected into HEK293 cells at 37° C. for 48 h. Subsequently, the cultures were stained with propidium iodide (PI) to visualize the nucleus. Finally, a comparative morphological examination of the individual cells in these cultures was performed to determine whether and how much cytotoxicity or apoptosis was observed in the transfected cells.

HEK293 cells were transfected with specific Nef constructs described above, and the cell populations were stained with PI. These cells were analyzed for GFP fluorescence (NefGFP expression), PI fluorescence (necrotic cells hallmark of cell death), and coincidence of PI and GFP (dying cells expressing Nef) in the cells (FIG. 8A). Endogenously expressed GFP fluorescence, a measure of Nef expression, for all treatments ranged between 70% and 80% and did not vary significantly. PI fluorescence, a measure of cell death, varied from 3% (pQBI-GFP; FIG. 8A, PI measure) in the negative control and the Nef mutants to ~12% (pQBI-NefGFP; FIG. 8A, PI measure) in the transfections with wtNef-GFP. Thus, wtNef-GFP protein expressed within the cells does increase the amount of cell death by about 4-fold with about half of that cell death occurring in the transfected cells (see FIG. 8A, wtNef-GFP, GFP/PI overlay measure). However, the total amount of cell death remained modest.

Figure 8B:
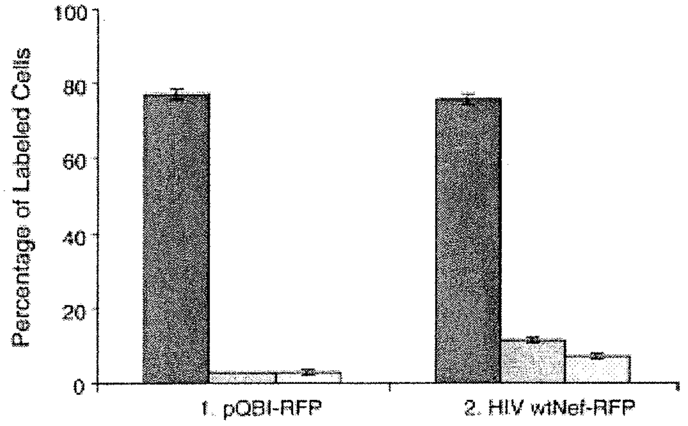

HEK293 cells were transfected with wild-type pQBI-Nef-RFP and then TUNEL labeled for detection or earlier signs of apoptosis in the form of DNA fragmentation. These cells were analyzed for RFP fluorescence (Nef-RFP expression), TUNEL (apoptosis), and the coincidence of RFP and TUNEL (apoptotic cells expressing Nef) in the cells (FIG. 8B). Endogenously expressed RFP fluorescence, a measure of Nef expression, for all treatments ranged between 75% and 80% and did not vary significantly. FITC fluorescence, in TUNEL-labeled apoptotic cells, ranged from 2% (pQBI-RFP, FIG. 8B, RFP measure) in the negative control to ~12% (pQBI-Nef-RFP, TUNEL measure) in the transfections with wtNef. Again, wtNef protein expressed within cells increased the amount of apoptosis by about 6-fold with half of that apoptosis occurring in the transfected cells (see FIG. 8B, wtNef-RFP, RFP/TUNEL overlay measure). Again, the total amount of cell death in the population was very modest.

Figure 9A:
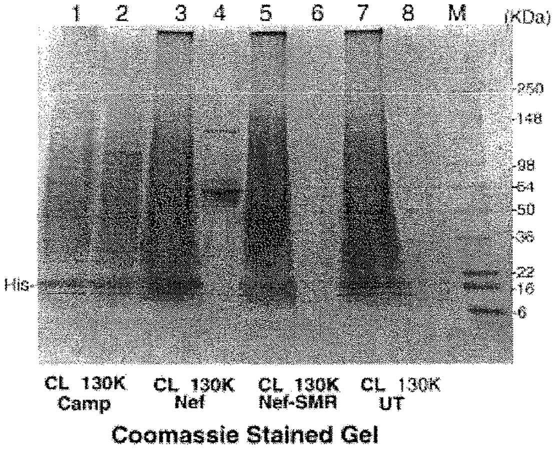
FIGS. 9A-B demonstrate that Nef-induced vesicles do not display attributes of apoptotic vesicles. HIV-1 wtNef-GFP and Nef-GFP mutants were transfected into HEK293 cells.

Thus, evidence for direct and indirect induction of apoptosis was present but minimal. Next, to see whether transfected cells released histone-containing apoptotic vesicles into the conditioned supernatant, HEK293 cells were either treated with camptothecin, an apoptosis-inducing factor (FIG. 9A, lanes 1 and 2), or transfected with pQBI-NefGFP (FIG. 9A, lanes 3 and 4), pQBI-$Nef^{66}VGFPV^{70}GFP$ (FIG. 9A, lanes 5 and 6), or pQBI-GFP (FIG. 9A, lanes 7 and 8). The 48 h cultures were harvested for the conditioned media and the cell lysates. The conditioned media from each treatment were subjected to differential centrifugation with four sequential centrifugation steps of 300×g, 1200×g, 10,000×g, and finally 130,000×g. A silver-stained SDS-PAGE analysis of the cell lysates (FIG. 9A, lanes 1, 3, 5, and 7) and 130,000×g pellets (FIG. 9A, lanes 2, 4, 6, and 8) was examined for the protein composition of those two fractions. The banding pattern in the camptothecin-treated cells (FIG. 9A, lanes 1 and 2) was distinct from the other three transfection treatments (FIG. 9A, lanes 3-8).

Figure 9B:
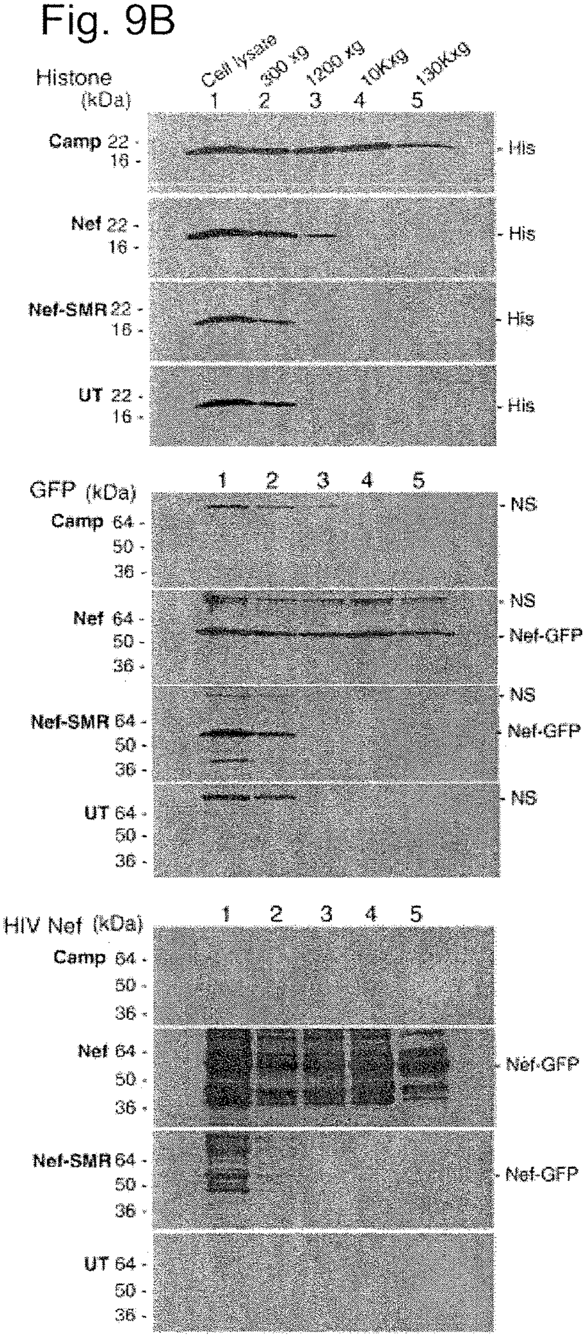

To specifically look at the histones in these treatment conditions, SDS-PAGE analyses of the cell lysate of each treatment and the pellets from each centrifugation step were screened by Western analysis (FIG. 9A). This was done with (1) a histone polyclonal antibody (FIG. 9B, first panel set) to screen and quantify histones, (2) a GFP antibody (FIG. 9B, second panel set), and (3) an HIV-1 Nef antibody (FIG. 9B, third panel set). The camptothecin-treated cells (FIG. 9B, histone set, panel one) displayed a histone band in both the cell lysate as well as in all four differential centrifugation-generated pellets as expected following camptothecin-induced apoptosis: histones were detected in both the cell lysates and vesicles released in the supernatants. In comparison, HEK293 transfected with pQBI expressing wtNef, SMR mutated Nef, or untransfected control, histone bands are detected only in the cell lysates and in the low-speed centrifugations (300×g and 1200×g) in which cellular debris is normally pelleted. This suggests that Nef transfection does not result in significant release of apoptotic histone-containing vesicles. The transfected and wtNef-GFP-expressing cultures analyzed by GFP antibodies (FIG. 9B, GFP set, panel two) or by Nef antibodies (FIG. 9B, Nef set, panel two) display Nef-GFP protein in both the cell lysate as well as in all four differential centrifugation conditions. This indicates that Nef is there in a high-molecular-weight format indicative of Nef-containing vesicles.

The evidence suggests that despite finding an increased (but small total) amount of cell death/apoptosis in the Nef-transfected cells, the vesicles released from these cultures have very little if any histones in them, suggesting a morphology distinct from apoptotic vesicles. Alternatively, they do have Nef-GFP in them, suggesting that the Nef-containing vesicles may be exosomes.

Figures 10A, 10B, 10C, 10D:
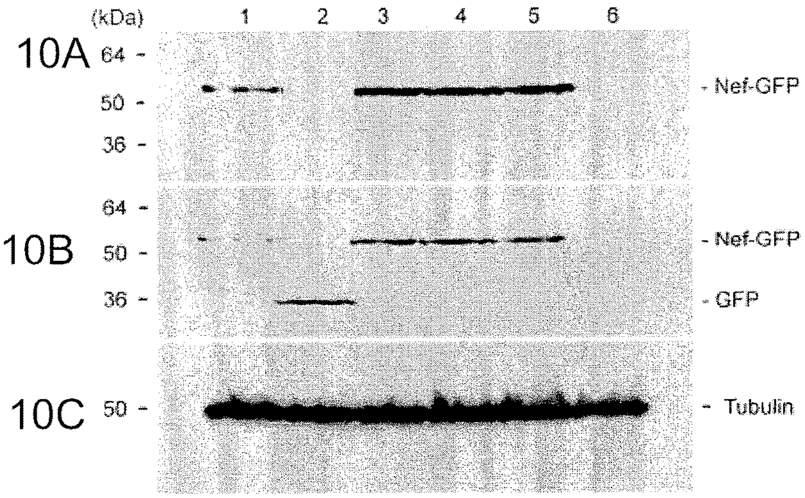
FIGS. 10A-D show that the effects of Nef mutants is not due to variable transfection/expression efficiencies.

The effect of Nef mutants was not due to variable expression. The effects observed in the various mutants could be due to variation in the ability of each clone to express the resultant fusion protein and not due to differences in their ability to secrete the fusion protein. This issue was addressed by examining the expression pattern of untransfected and transfected HEK293 cells by Western analysis of whole cell extracts probed with anti-Nef antibody (FIG. 10A) or anti-GFP antibody (FIG. 10B). Cultures were transfected with pQBI-Nef-GFP (Nef-GFP; FIG. 10, lane 1), pQBI-GFP (GFP; FIG. 10, lane 2), pQBI-Nef$^{62}$EEEE$^{65}$/4AGFP (PACS; FIG. 10, lane 3), pQBI-NefV66/A (SMR AGFPV, FIG. 10, lane 4), pQBI-Nef$^{17,19,21,22}$R/4AGFP (Basic Region 2, FIG. 10, lane 5), or untransfected (FIG. 10, lane 6). FIG. 10D is the densitometric analysis of FIGS. 10A-C. The Nef and GFP band densities in the mutant expressing cultures are similar (FIG. 10D). Alternatively, a significant difference was observed in the band densities of wtNef-GFP-expressing cells vs. the Nef mutant-expressing cells (FIG. 10D, wtNef-GFP vs. all others). This suggests that NefGFP protein made and released in the wtNef-GFP-expressing cells accumulates within the mutant Nef-GFP-expressing cells.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A Nef-fusion protein comprising a Nef-derived peptide fused to a protein of interest, wherein the Nef-derived peptide consists of either SEQ ID NO:3 or SEQ ID NO:4.

2. The Nef-fusion protein of claim 1, wherein the protein of interest is an immunotherapeutic protein.

3. The Nef-fusion protein of claim 2, wherein the immunotherapeutic protein is an immunosuppressive protein.

4. The Nef-fusion protein of claim 1, wherein the protein of interest is an immunogenic protein.

5. The Nef-fusion protein of claim 4, wherein the immunogenic protein comprises at least a portion of a tumor antigen.

6. The Nef-fusion protein of claim 1, further comprising one or more functional domains.

7. The Nef-fusion protein of claim 6, wherein the one or more functional domains are selected from the group consisting of affinity tags, protease cleavage sites, targeting domains, reporters and enzymes.

8. The Nef-fusion protein of claim 6, wherein the one or more functional domains comprise one or more affinity tags selected from the group consisting of glutathione S-transferase (GST), histidine tag, maltose binding protein (MBP), protein A, thioredoxin, ubiquitin, biotin, calmodulin binding peptide (CBP), streptavidin tag, FLAG octapeptide tag, hemaglutinin A (HA) tag, and mye tag.

9. The Nef-fusion protein of claim 6, wherein the one or more functional domains comprise one or more protease cleavage sites selected from the group consisting of cleavage sites sensitive to thrombin, furin, factor Xa, metalloproteases, enterokinases, or cathepsin.

10. The Nef-fusion protein of claim 6, wherein the one or more functional domains comprise one or more targeting domains selected from the group consisting or antibodies, antibody derivatives, peptide ligands, receptor ligands, receptor fragments and hormones.

11. A pharmaceutical composition comprising the Nef-fusion protein of claim 1 and a pharmaceutically acceptable carrier.

* * * * *

SEQUENCE LISTING

```
<160> NUMBER OF SEQ ID NOS: 52

<210> SEQ ID NO 1
<211> LENGTH: 206
<212> TYPE: PRT
<213> ORGANISM: Human immunodeficiency virus type 1

<400> SEQUENCE: 1

Met Gly Gly Lys Trp Ser Lys Ser Ser Val Ile Gly Trp Pro Ala Val
1               5                   10                  15

Arg Glu Arg Met Arg Arg Ala Glu Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ala Asn Asn Ala Ala Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205


<210> SEQ ID NO 2
<211> LENGTH: 263
<212> TYPE: PRT
```

-continued

<213> ORGANISM: Simian immunodeficiency virus

<400> SEQUENCE: 2

```
Met Gly Gly Ala Ile Ser Met Arg Arg Ser Arg Pro Ser Gly Asp Leu
1               5                   10                  15

Arg Gln Arg Leu Leu Arg Ala Arg Gly Glu Thr Tyr Gly Arg Leu Leu
            20                  25                  30

Gly Glu Val Glu Asp Gly Tyr Ser Gln Ser Pro Gly Gly Leu Asp Lys
        35                  40                  45

Gly Leu Ser Ser Leu Ser Cys Glu Gly Gln Lys Tyr Asn Gln Gly Gln
    50                  55                  60

Tyr Met Asn Thr Pro Trp Arg Asn Pro Ala Glu Lys Arg Glu Lys Leu
65                  70                  75                  80

Ala Tyr Arg Lys Gln Asn Met Asp Asp Ile Asp Glu Glu Asp Asn Asp
                85                  90                  95

Leu Val Gly Val Ser Val Trp Pro Arg Val Pro Leu Arg Thr Met Ser
            100                 105                 110

Tyr Lys Leu Ala Ile Asp Met Ser His Phe Ile Lys Glu Lys Gly Gly
        115                 120                 125

Leu Glu Gly Ile Tyr Tyr Ser Glu Arg Arg His Arg Ile Leu Asp Ile
    130                 135                 140

Tyr Leu Glu Lys Glu Glu Gly Ile Ile Pro Asp Trp Gln Asp Tyr Thr
145                 150                 155                 160

Ser Gly Pro Gly Ile Arg Tyr Pro Lys Thr Phe Gly Trp Leu Trp Lys
                165                 170                 175

Leu Val Pro Val Asn Val Ser Asp Glu Ala Gln Glu Asp Glu Glu His
            180                 185                 190

Cys Leu Ile His Pro Ala Gln Thr Ser Gln Trp Asp Asp Pro Trp Gly
        195                 200                 205

Glu Val Leu Ala Trp Lys Phe Asp Pro Thr Leu Ala Tyr Thr His Glu
    210                 215                 220

Ala Tyr Val Arg Tyr Pro Glu Glu Phe Gly Ser Lys Ser Gly Leu Ser
225                 230                 235                 240

Glu Glu Glu Val Arg Arg Arg Leu Thr Ala Arg Gly Leu Leu Asn Met
                245                 250                 255

Ala Asp Lys Lys Glu Thr Arg
            260
```

<210> SEQ ID NO 3
<211> LENGTH: 29
<212> TYPE: PRT
<213> ORGANISM: Human immunodeficiency virus type 1

<400> SEQUENCE: 3

```
Trp Pro Ala Val Arg Glu Arg Met Arg Arg Ala Glu Pro Ala Ala Asp
1               5                   10                  15

Gly Val Gly Ala Val Ser Arg Asp Leu Glu Lys His Gly
            20                  25
```

<210> SEQ ID NO 4
<211> LENGTH: 102
<212> TYPE: PRT
<213> ORGANISM: Simian immunodeficiency virus

<400> SEQUENCE: 4

```
Met Gly Gly Ala Ile Ser Met Arg Arg Ser Arg Pro Ser Gly Asp Leu
1               5                   10                  15
```

```
Arg Gln Arg Leu Leu Arg Ala Arg Gly Glu Thr Tyr Gly Arg Leu Leu
            20                  25                  30

Gly Glu Val Glu Asp Gly Tyr Ser Gln Ser Pro Gly Gly Leu Asp Lys
        35                  40                  45

Gly Leu Ser Ser Leu Ser Cys Glu Gly Gln Lys Tyr Asn Gln Gly Gln
    50                  55                  60

Tyr Met Asn Thr Pro Trp Arg Asn Pro Ala Glu Lys Arg Glu Lys Leu
65                  70                  75                  80

Ala Tyr Arg Lys Gln Asn Met Asp Asp Ile Asp Glu Glu Asp Asn Asp
                85                  90                  95

Leu Val Gly Val Ser Val
            100


<210> SEQ ID NO 5
<211> LENGTH: 58
<212> TYPE: PRT
<213> ORGANISM: Human immunodeficiency virus type 1

<400> SEQUENCE: 5

Trp Pro Ala Val Arg Glu Arg Met Arg Arg Ala Glu Pro Ala Ala Asp
1               5                   10                  15

Gly Val Gly Ala Val Ser Arg Asp Leu Glu Lys His Gly Ala Ile Thr
            20                  25                  30

Ser Ser Asn Thr Ala Ala Asn Asn Ala Ala Cys Ala Trp Leu Glu Ala
        35                  40                  45

Gln Glu Glu Glu Glu Val Gly Phe Pro Val
    50                  55


<210> SEQ ID NO 6
<211> LENGTH: 70
<212> TYPE: PRT
<213> ORGANISM: Human immunodeficiency virus type 1

<400> SEQUENCE: 6

Met Gly Gly Lys Trp Ser Lys Ser Ser Val Ile Gly Trp Pro Ala Val
1               5                   10                  15

Arg Glu Arg Met Arg Arg Ala Glu Pro Ala Ala Asp Gly Val Gly Ala
            20                  25                  30

Val Ser Arg Asp Leu Glu Lys His Gly Ala Ile Thr Ser Ser Asn Thr
        35                  40                  45

Ala Ala Asn Asn Ala Ala Cys Ala Trp Leu Glu Ala Gln Glu Glu Glu
    50                  55                  60

Glu Val Gly Phe Pro Val
65                  70


<210> SEQ ID NO 7
<211> LENGTH: 20
<212> TYPE: PRT
<213> ORGANISM: Artificial Sequence
<220> FEATURE:
<223> OTHER INFORMATION: synthesized
<220> FEATURE:
<221> NAME/KEY: MISC_FEATURE
<222> LOCATION: (1)..(20)
<223> OTHER INFORMATION: Positions 1 to 4 have between 1 to 4 Gly
      Position 5 is Ala or Ser       Positions 1-5 define a unit that
      can be present 1 to 4 times
<220> FEATURE:
<221> NAME/KEY: MISC_FEATURE
<222> LOCATION: (1)..(20)
<223> OTHER INFORMATION: Positions 1 to 4 have between 1 to 4 Gly
```

-continued

In position 5, Xaa is Ala or Ser Positions 1-5 define a unit that can be present 1 to 4 times

<400> SEQUENCE: 7

```
Gly Gly Gly Gly Xaa Gly Gly Gly Gly Xaa Gly Gly Gly Gly Xaa Gly
1               5                   10                  15

Gly Gly Gly Xaa
            20
```

<210> SEQ ID NO 8
<211> LENGTH: 27
<212> TYPE: DNA
<213> ORGANISM: Artificial Sequence
<220> FEATURE:
<223> OTHER INFORMATION: synthesized

<400> SEQUENCE: 8
cgtgtacggt gggaggtcta tataagc 27

<210> SEQ ID NO 9
<211> LENGTH: 23
<212> TYPE: DNA
<213> ORGANISM: Artificial Sequence
<220> FEATURE:
<223> OTHER INFORMATION: synthesized

<400> SEQUENCE: 9
cataaccttc gggcatggca ctc 23

<210> SEQ ID NO 10
<211> LENGTH: 31
<212> TYPE: DNA
<213> ORGANISM: Artificial Sequence
<220> FEATURE:
<223> OTHER INFORMATION: synthesized

<400> SEQUENCE: 10
cattgctagc cccatctgct gctggctcag c 31

<210> SEQ ID NO 11
<211> LENGTH: 37
<212> TYPE: DNA
<213> ORGANISM: Artificial Sequence
<220> FEATURE:
<223> OTHER INFORMATION: synthesized

<400> SEQUENCE: 11
cattgctagc agctgctgta ttgctacttg tgattgc 37

<210> SEQ ID NO 12
<211> LENGTH: 35
<212> TYPE: DNA
<213> ORGANISM: Artificial Sequence
<220> FEATURE:
<223> OTHER INFORMATION: synthesized

<400> SEQUENCE: 12
cattgctagc ctcttcctcc tcttgtgctt ctagc 35

<210> SEQ ID NO 13
<211> LENGTH: 34
<212> TYPE: DNA
<213> ORGANISM: Artificial Sequence
<220> FEATURE:
<223> OTHER INFORMATION: synthesized

<400> SEQUENCE: 13
cattgctagc gactggaaaa cccacctctt cctc 34

<210> SEQ ID NO 14
<211> LENGTH: 37
<212> TYPE: DNA
<213> ORGANISM: Artificial Sequence
<220> FEATURE:
<223> OTHER INFORMATION: synthesized

<400> SEQUENCE: 14
cattgctagc aaagtggcta agatctacag ctgcctt 37

<210> SEQ ID NO 15
<211> LENGTH: 37
<212> TYPE: DNA
<213> ORGANISM: Artificial Sequence
<220> FEATURE:
<223> OTHER INFORMATION: synthesized

<400> SEQUENCE: 15
cattgctagc tggctcaact ggtactagct tgtagca 37

<210> SEQ ID NO 16
<211> LENGTH: 30
<212> TYPE: DNA
<213> ORGANISM: Artificial Sequence
<220> FEATURE:
<223> OTHER INFORMATION: synthesized

<400> SEQUENCE: 16
cattgctagc cggatgcagc tctcgggcca 30

<210> SEQ ID NO 17
<211> LENGTH: 24
<212> TYPE: DNA
<213> ORGANISM: Artificial Sequence
<220> FEATURE:
<223> OTHER INFORMATION: synthesized

<400> SEQUENCE: 17
ggtcctccga tcgttgtcag aagt 24

<210> SEQ ID NO 18
<211> LENGTH: 37
<212> TYPE: DNA
<213> ORGANISM: Artificial Sequence
<220> FEATURE:
<223> OTHER INFORMATION: synthesized

<400> SEQUENCE: 18
cagtccgcgg atgtggcctg ctgtaaggga aagaatg 37

<210> SEQ ID NO 19
<211> LENGTH: 40
<212> TYPE: DNA
<213> ORGANISM: Artificial Sequence
<220> FEATURE:
<223> OTHER INFORMATION: synthesized

<400> SEQUENCE: 19
cagtccgcgg atgggagcaa tcacaagtag caatacagca 40

<210> SEQ ID NO 20
<211> LENGTH: 36

<212> TYPE: DNA
<213> ORGANISM: Artificial Sequence
<220> FEATURE:
<223> OTHER INFORMATION: synthesized

<400> SEQUENCE: 20
ctagaagcac aagcggcggc agcggtgggt tttcca 36

<210> SEQ ID NO 21
<211> LENGTH: 36
<212> TYPE: DNA
<213> ORGANISM: Artificial Sequence
<220> FEATURE:
<223> OTHER INFORMATION: synthesized

<400> SEQUENCE: 21
tggaaaaccc accgctgccg ccgcttgtgc ttctag 36

<210> SEQ ID NO 22
<211> LENGTH: 45
<212> TYPE: DNA
<213> ORGANISM: Artificial Sequence
<220> FEATURE:
<223> OTHER INFORMATION: synthesized

<400> SEQUENCE: 22
atgtggcctg ctgtagcgga agcaatggca gcagctgagc cagca 45

<210> SEQ ID NO 23
<211> LENGTH: 45
<212> TYPE: DNA
<213> ORGANISM: Artificial Sequence
<220> FEATURE:
<223> OTHER INFORMATION: synthesized

<400> SEQUENCE: 23
tgctggctca gctgctgcca ttgcttccgc tacagcaggc cacat 45

<210> SEQ ID NO 24
<211> LENGTH: 45
<212> TYPE: DNA
<213> ORGANISM: Artificial Sequence
<220> FEATURE:
<223> OTHER INFORMATION: synthesized

<400> SEQUENCE: 24
gcagtatctc gagacctaga accgcatgga gcaatcacaa gtagc 45

<210> SEQ ID NO 25
<211> LENGTH: 45
<212> TYPE: DNA
<213> ORGANISM: Artificial Sequence
<220> FEATURE:
<223> OTHER INFORMATION: synthesized

<400> SEQUENCE: 25
gctacttgtg attgctccat gcggttctag gtctcgagat actgc 45

<210> SEQ ID NO 26
<211> LENGTH: 36
<212> TYPE: DNA
<213> ORGANISM: Artificial Sequence
<220> FEATURE:
<223> OTHER INFORMATION: synthesized

<400> SEQUENCE: 26

-continued catggagcaa tcacagccgc gaatacagca gctaac 36

<210> SEQ ID NO 27
<211> LENGTH: 36
<212> TYPE: DNA
<213> ORGANISM: Artificial Sequence
<220> FEATURE:
<223> OTHER INFORMATION: synthesized

<400> SEQUENCE: 27
gttagctgct gtattcgcgg ctgtgattgc tccatg 36

<210> SEQ ID NO 28
<211> LENGTH: 42
<212> TYPE: DNA
<213> ORGANISM: Artificial Sequence
<220> FEATURE:
<223> OTHER INFORMATION: synthesized

<400> SEQUENCE: 28
tggctagaag cacaagacga cgacgacgtg ggttttccag tc 42

<210> SEQ ID NO 29
<211> LENGTH: 42
<212> TYPE: DNA
<213> ORGANISM: Artificial Sequence
<220> FEATURE:
<223> OTHER INFORMATION: synthesized

<400> SEQUENCE: 29
gactggaaaa cccacgtcgt cgtcgtcttg tgcttctagc ca 42

<210> SEQ ID NO 30
<211> LENGTH: 45
<212> TYPE: DNA
<213> ORGANISM: Artificial Sequence
<220> FEATURE:
<223> OTHER INFORMATION: synthesized

<400> SEQUENCE: 30
caagaggagg aagaggcggc tgctgcagcc gctagcaaag gagaa 45

<210> SEQ ID NO 31
<211> LENGTH: 45
<212> TYPE: DNA
<213> ORGANISM: Artificial Sequence
<220> FEATURE:
<223> OTHER INFORMATION: synthesized

<400> SEQUENCE: 31
ttctcctttg ctagcggctg cagcagccgc ctcttcctcc tcttg 45

<210> SEQ ID NO 32
<211> LENGTH: 40
<212> TYPE: DNA
<213> ORGANISM: Artificial Sequence
<220> FEATURE:
<223> OTHER INFORMATION: synthesized

<400> SEQUENCE: 32
cagtccgcgg atggctagca aaggagaaga actcttcact 40

<210> SEQ ID NO 33
<211> LENGTH: 21
<212> TYPE: DNA
<213> ORGANISM: Artificial Sequence
<220> FEATURE:
<223> OTHER INFORMATION: synthesized

<400> SEQUENCE: 33
tgcagaattc cagcacactg g 21

<210> SEQ ID NO 34
<211> LENGTH: 40
<212> TYPE: DNA
<213> ORGANISM: Artificial Sequence
<220> FEATURE:
<223> OTHER INFORMATION: synthesized

<400> SEQUENCE: 34
cagtccgcgg atggctagca aaggagaaga actcttcact 40

<210> SEQ ID NO 35
<211> LENGTH: 21
<212> TYPE: DNA
<213> ORGANISM: Artificial Sequence
<220> FEATURE:
<223> OTHER INFORMATION: synthesized

<400> SEQUENCE: 35
tgcagaattc cagcacactg g 21

<210> SEQ ID NO 36
<211> LENGTH: 37
<212> TYPE: DNA
<213> ORGANISM: Artificial Sequence
<220> FEATURE:
<223> OTHER INFORMATION: synthesized

<400> SEQUENCE: 36
cgcggctagc tcatctgtga gcaagggcga ggaggat 37

<210> SEQ ID NO 37
<211> LENGTH: 34
<212> TYPE: DNA
<213> ORGANISM: Artificial Sequence
<220> FEATURE:
<223> OTHER INFORMATION: synthesized

<400> SEQUENCE: 37
cgcgggatcc tcacttgtac agctcgtcca tgcc 34

<210> SEQ ID NO 38
<211> LENGTH: 34
<212> TYPE: DNA
<213> ORGANISM: Artificial Sequence
<220> FEATURE:
<223> OTHER INFORMATION: synthesized

<400> SEQUENCE: 38
cgcgaagctt atggtgagca agggcgagga ggat 34

<210> SEQ ID NO 39
<211> LENGTH: 209
<212> TYPE: PRT
<213> ORGANISM: Human immunodeficiency virus type 1

<400> SEQUENCE: 39

Met Gly Gly Lys Trp Ser Lys Ser Ser Val Ile Gly Trp Pro Ala Val
1               5                   10                  15

Arg Glu Arg Met Arg Arg Ala Glu Pro Ala Ala Asp Gly Val Gly Ala

-continued

```
            20                  25                  30

Val Ser Arg Asp Leu Glu Lys His Gly Ala Ile Thr Ser Ser Asn Thr
        35                  40                  45

Ala Ala Asn Asn Ala Ala Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Val Arg Tyr Pro Leu Thr Phe Gly Trp Cys Tyr Lys
    130                 135                 140

Leu Val Pro Val Glu Pro Asp Lys Val Glu Glu Ala Asn Lys Gly Glu
145                 150                 155                 160

Asn Thr Ser Leu Leu His Pro Val Ser Leu His Gly Met Asp Asp Pro
                165                 170                 175

Glu Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys Gly Ala
        195                 200                 205

Gly


<210> SEQ ID NO 40
<211> LENGTH: 10
<212> TYPE: PRT
<213> ORGANISM: Human immunodeficiency virus type 1

<400> SEQUENCE: 40

Gln Glu Glu Glu Glu Val Gly Phe Pro Val
1               5                   10


<210> SEQ ID NO 41
<211> LENGTH: 11
<212> TYPE: PRT
<213> ORGANISM: Human immunodeficiency virus type 1

<400> SEQUENCE: 41

Gln Glu Glu Glu Glu Glu Val Gly Phe Pro Val
1               5                   10


<210> SEQ ID NO 42
<211> LENGTH: 10
<212> TYPE: PRT
<213> ORGANISM: Human immunodeficiency virus type 1

<400> SEQUENCE: 42

Gln Glu Glu Glu Glu Val Gly Phe Pro Val
1               5                   10


<210> SEQ ID NO 43
<211> LENGTH: 11
<212> TYPE: PRT
<213> ORGANISM: Human immunodeficiency virus type 1

<400> SEQUENCE: 43

Gln Glu Glu Glu Glu Glu Val Gly Phe Pro Val
```

1 5 10

<210> SEQ ID NO 44
<211> LENGTH: 11
<212> TYPE: PRT
<213> ORGANISM: Human immunodeficiency virus type 1

<400> SEQUENCE: 44

Gln Glu Glu Glu Glu Glu Val Gly Phe Pro Val
1 5 10

<210> SEQ ID NO 45
<211> LENGTH: 10
<212> TYPE: PRT
<213> ORGANISM: Human immunodeficiency virus type 1

<400> SEQUENCE: 45

Gln Glu Glu Glu Glu Val Gly Phe Pro Val
1 5 10

<210> SEQ ID NO 46
<211> LENGTH: 10
<212> TYPE: PRT
<213> ORGANISM: Human immunodeficiency virus type 1

<400> SEQUENCE: 46

Gln Glu Asp Glu Glu Val Gly Phe Pro Val
1 5 10

<210> SEQ ID NO 47
<211> LENGTH: 11
<212> TYPE: PRT
<213> ORGANISM: Human immunodeficiency virus type 1

<400> SEQUENCE: 47

Gln Gln Glu Asp Ser Glu Val Gly Phe Pro Val
1 5 10

<210> SEQ ID NO 48
<211> LENGTH: 11
<212> TYPE: PRT
<213> ORGANISM: Human immunodeficiency virus type 1

<400> SEQUENCE: 48

Gln Glu Glu Glu Glu Glu Val Gly Phe Pro Val
1 5 10

<210> SEQ ID NO 49
<211> LENGTH: 10
<212> TYPE: PRT
<213> ORGANISM: Human immunodeficiency virus type 1

<400> SEQUENCE: 49

Gln Thr Glu Glu Glu Val Gly Phe Pro Val
1 5 10

<210> SEQ ID NO 50
<211> LENGTH: 10
<212> TYPE: PRT
<213> ORGANISM: Human immunodeficiency virus type 1

<400> SEQUENCE: 50

Gln Glu Glu Glu Glu Val Gly Phe Pro Val
1 5 10

-continued

```
<210> SEQ ID NO 51
<211> LENGTH: 11
<212> TYPE: PRT
<213> ORGANISM: Human immunodeficiency virus type 1

<400> SEQUENCE: 51

Gln Glu Glu Glu Glu Glu Val Gly Phe Pro Val
1               5                   10


<210> SEQ ID NO 52
<211> LENGTH: 10
<212> TYPE: PRT
<213> ORGANISM: Human immunodeficiency virus type 1

<400> SEQUENCE: 52

His Gln Asp Glu Glu Val Gly Phe Pro Val
1               5                   10
```